US010682631B2

(12) United States Patent
Amakawa et al.

(10) Patent No.: US 10,682,631 B2
(45) Date of Patent: Jun. 16, 2020

(54) MULTIMETAL OXIDE COMPOSITIONS COMPRISING MO, BI, FE AND CU

(71) Applicant: BASF SE, Ludwigshafen am Rhein (DE)

(72) Inventors: Kazuhiko Amakawa, Ludwigshafen (DE); Christian Walsdorff, Ludwigshafen (DE); Klaus Joachim Mueller-Engel, Ludwigshafen (DE); Cornelia Katharina Dobner, Ludwigshafen (DE); Ulrich Hammon, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/250,244

(22) Filed: Jan. 17, 2019

(65) Prior Publication Data

US 2019/0224651 A1 Jul. 25, 2019

(30) Foreign Application Priority Data

Jan. 19, 2018 (DE) .................. 10 2018 200 841

(51) Int. Cl.
| | | |
|---|---|---|
| *B01J 23/00* | (2006.01) | |
| *B01J 35/00* | (2006.01) | |
| *B01J 37/00* | (2006.01) | |
| *C07C 45/35* | (2006.01) | |
| *B01J 23/887* | (2006.01) | |
| *C07C 51/215* | (2006.01) | |
| *B01J 35/10* | (2006.01) | |
| *B01J 23/888* | (2006.01) | |
| *B01J 37/08* | (2006.01) | |
| *B01J 37/02* | (2006.01) | |
| *C01G 39/00* | (2006.01) | |
| *B01J 35/02* | (2006.01) | |
| *B01J 37/04* | (2006.01) | |
| *C01B 33/32* | (2006.01) | |

(52) U.S. Cl.
CPC ......... *B01J 23/8876* (2013.01); *B01J 23/002* (2013.01); *B01J 23/8885* (2013.01); *B01J 35/008* (2013.01); *B01J 35/026* (2013.01); *B01J 35/1009* (2013.01); *B01J 35/1038* (2013.01); *B01J 35/1042* (2013.01); *B01J 37/0018* (2013.01); *B01J 37/0236* (2013.01); *B01J 37/04* (2013.01); *B01J 37/08* (2013.01); *B01J 37/088* (2013.01); *C01B 33/32* (2013.01); *C01G 39/006* (2013.01); *C07C 45/35* (2013.01); *C07C 51/215* (2013.01); *B01J 2523/00* (2013.01); *C01P 2002/50* (2013.01); *C01P 2004/30* (2013.01)

(58) Field of Classification Search
CPC .... C07C 45/35; B01L 23/8876; B01L 35/008; B01L 37/08; C01B 33/32
See application file for complete search history.

(56) References Cited

U.S. PATENT DOCUMENTS

| | | | |
|---|---|---|---|
| 3,951,861 | A | 4/1976 | Shiraishi et al. |
| 3,992,419 | A | 11/1976 | Otaki et al. |
| 2005/0131253 | A1 | 6/2005 | Teshigahara et al. |
| 2014/0171303 | A1 | 6/2014 | Yoshida et al. |

FOREIGN PATENT DOCUMENTS

| | | |
|---|---|---|
| CN | 101168129 A | 4/2008 |
| CN | 102247862 A | 11/2011 |
| CN | 102989471 A | 3/2013 |
| CN | 104646012 A | 5/2015 |
| DE | 25 16 966 A1 | 10/1975 |
| DE | 29 09 671 A1 | 10/1980 |
| DE | 44 07 020 A1 | 9/1994 |
| DE | 44 31 957 A1 | 3/1995 |
| DE | 44 42 346 A1 | 5/1996 |
| DE | 198 55 913 A1 | 6/2000 |
| DE | 199 10 506 A1 | 9/2000 |
| DE | 199 48 248 A1 | 4/2001 |
| DE | 199 48 523 A1 | 4/2001 |
| DE | 100 46 957 A1 | 4/2002 |
| DE | 100 49 873 A1 | 4/2002 |
| DE | 100 59 713 A1 | 6/2002 |
| DE | 100 63 162 A1 | 6/2002 |
| DE | 102 32 482 A1 | 1/2004 |
| DE | 103 13 209 A1 | 3/2004 |
| DE | 102 45 585 A1 | 4/2004 |
| DE | 102 46 119 A1 | 4/2004 |
| DE | 103 13 208 A1 | 10/2004 |
| DE | 103 13 213 A1 | 10/2004 |
| DE | 103 37 788 A1 | 10/2004 |
| DE | 10 2005 037 678 A1 | 2/2007 |
| DE | 10 2007 005 606 A1 | 4/2008 |
| DE | 10 2007 003 076 A1 | 7/2008 |
| DE | 10 2007 004 961 A1 | 7/2008 |
| DE | 10 2008 040 093 A1 | 12/2008 |
| DE | 10 2008 040 094 A1 | 1/2009 |
| DE | 10 2008 042 060 A1 | 6/2009 |
| DE | 10 2008 042 061 A1 | 3/2010 |
| DE | 10 2008 042 064 A1 | 3/2010 |

(Continued)

OTHER PUBLICATIONS

International Search Report dated Apr. 26, 2019 in PCT/EP2019/050292, citing documents AA-AB and AO-AP therein, 4 pages (with English Translation of Category of Cited Documents).

*Primary Examiner* — Sikarl A Witherspoon

(74) *Attorney, Agent, or Firm* — Oblon, McClelland, Maier & Neustadt, L.L.P.

(57) ABSTRACT

Multimetal oxide composition comprising Mo, Bi, Fe, Cu and one or more than one of the elements Co and Ni and use thereof.

15 Claims, 1 Drawing Sheet

(56) References Cited

FOREIGN PATENT DOCUMENTS

| | | |
|---|---|---|
| DE | 10 2008 054 586 A1 | 6/2010 |
| DE | 10 2009 047 291 A1 | 9/2010 |
| DE | 10 2010 048 405 A1 | 5/2011 |
| EP | 0 184 790 A2 | 6/1986 |
| EP | 0 293 859 A1 | 12/1988 |
| EP | 0 468 290 B1 | 1/1992 |
| EP | 0 575 897 A1 | 12/1993 |
| EP | 0 700 714 A1 | 3/1996 |
| EP | 0 700 893 A1 | 3/1996 |
| EP | 0 714 700 A2 | 6/1996 |
| EP | 0 873 783 A1 | 10/1998 |
| EP | 0 990 636 A1 | 4/2000 |
| EP | 1 106 598 A2 | 6/2001 |
| EP | 2 727 648 A1 | 5/2014 |
| WO | WO 00/53557 | 9/2000 |
| WO | WO 00/53558 | 9/2000 |
| WO | WO 01/36364 A1 | 5/2001 |
| WO | WO 02/24620 A2 | 3/2002 |
| WO | WO 02/49757 A2 | 6/2002 |
| WO | WO 02/062737 A2 | 8/2002 |
| WO | WO 2004/007405 A1 | 1/2004 |
| WO | WO 2005/030393 A1 | 4/2005 |
| WO | WO 2005/042459 A1 | 5/2005 |
| WO | WO 2005/047224 A1 | 5/2005 |
| WO | WO 2005/113127 A1 | 12/2005 |
| WO | WO 2006/042459 A1 | 4/2006 |
| WO | WO 2007/017431 A1 | 2/2007 |
| WO | WO 2007/074045 A1 | 7/2007 |
| WO | WO 2007/082827 A1 | 7/2007 |
| WO | WO 2008/087116 A1 | 7/2008 |
| WO | WO 2010/066645 A2 | 6/2010 |
| WO | WO 2012/049246 A2 | 4/2012 |
| WO | WO 2013/007736 A1 | 1/2013 |
| WO | WO 2015/067656 A1 | 5/2015 |
| WO | WO 2016/147324 A1 | 9/2016 |

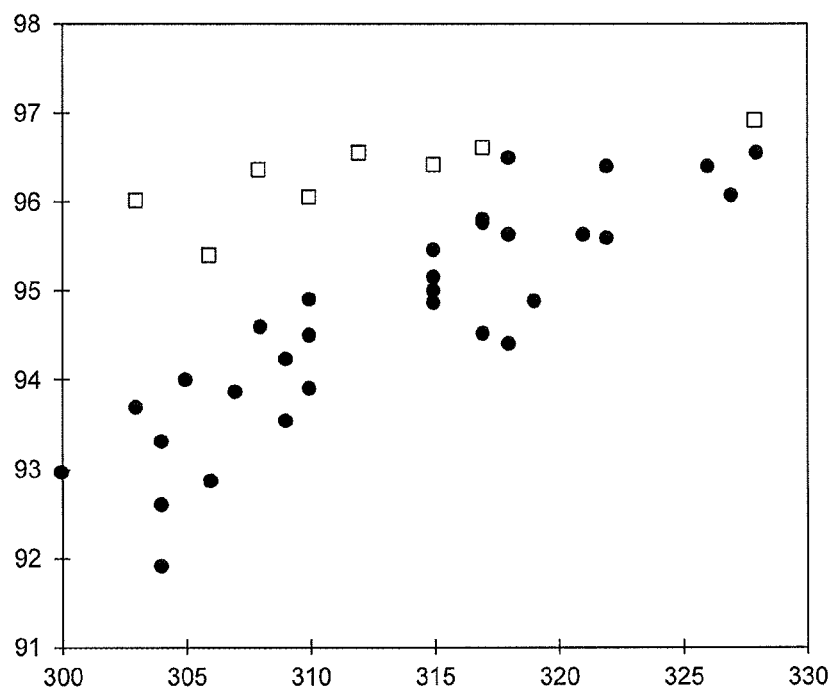

MULTIMETAL OXIDE COMPOSITIONS COMPRISING MO, BI, FE AND CU

The present invention relates to multimetal oxide compositions comprising Mo, Bi, Fe and Cu and having the general stoichiometry I $$Mo_{12}Bi_aFe_bCu_cCo_dNi_eW_fG_gH_hL_lM_mO_x \quad (I)$$

in which the variables are each defined as follows:
G=one element or more than one element from the group consisting of K, Na, Rb and Cs,
H=one element or more than one element from the group consisting of Ba, Ca, Cr, Ce, La, Mg, Mn, Pb, Sn, Sr and Zn,
L=one element or more than one element from the group consisting of B, Nb, P, Sb, Ta, Te, Ti, Y and Zr,
M=one element or more than one element from the group consisting of Al and Si,
a=0.2 to 2.5,
b=0.5 to 4,
c=0.05 to 0.55,
d+e=4 to 11,
f=0 to 1.2,
g=0.03 to 0.5,
h=0 to 20,
l=0 to 10,
m=0 to 800, and
x=a number which is determined by the valency and frequency of the elements in I other than oxygen,
and fulfill the following conditions:

$$12/(d+e+1.5 \cdot b+h)=0.8 \text{ to } 2, \text{ and}$$

$$a \cdot c=0.01 \text{ to } 1.5.$$

The present invention also relates to processes for producing multimetal oxide compositions of the general stoichiometry I and to the use thereof as catalytically active compositions of catalysts for the heterogeneously catalyzed partial gas phase oxidation of organic compounds, especially that of propene to acrolein as main product and acrylic acid as by-product.

In this document, the term "multimetal oxide" does not mean a simple mixture of different metal oxides, but means a complex polyoxy compound which, as well as oxygen, comprises elements of the general stoichiometry I in the desired individual stoichiometry. Semimetals such as B, P or Si are counted among the metals here for reasons of convenience.

Multimetal oxide compositions comprising Mo, Bi and Fe and having a stoichiometry similar to the general stoichiometry I are known, for example, from WO 2013/007736.

WO 2013/007736 also discloses using the multimetal oxide compositions disclosed therein as active compositions for the heterogeneously catalyzed partial gas phase oxidation of propene to acrolein as main product and acrylic acid as desired by-product (acrylic acid is a desired by-product especially because the heterogeneously catalyzed partial gas phase oxidation of propene to acrolein finds use in particular as the first oxidation stage in the two-stage partial oxidation of propene to acrylic acid).

However, a particular disadvantage of the multimetal oxide compositions of WO 2013/007736 as active compositions of catalysts for the heterogeneously catalyzed partial gas phase oxidation of propene to acrolein as main product and acrylic acid as desired by-product is that the overall selectivity of formation of acrolein and acrylic acid that results with these multimetal oxide compositions is not fully satisfactory.

The statements made with regard to the multimetal oxide compositions of WO 2013/007736 also relates to the multimetal oxide compositions comprising Mo, Bi and Fe of DE-A 19855913, of DE-A 10063162, of DE-A 102005037678, of DE-A 10059713, of DE-A 10049873, of DE-A 102007003076, of DE-A 102008054586, of DE-A 102007005606 and of DE-A 102007004961.

It was therefore one object of the present invention to provide multimetal oxide compositions comprising Mo, Bi and Fe which enable, as active compositions of catalysts for the heterogeneously catalyzed partial gas phase oxidation of propene to acrolein as main product and acrylic acid as by-product, an improved overall selectivity of formation of acrolein and acrylic acid (i.e. improved overall selectivity for products of value).

A disadvantage of this object is that measures for improving the aforementioned selectivity are known to impair the activity of the corresponding catalysts, generally to a perceptible degree.

It was therefore a further object of the present invention to provide multimetal oxide compositions comprising Mo, Bi and Fe which enable, as active compositions of catalysts for the heterogeneously catalyzed partial gas phase oxidation of propene to acrolein as main product and acrylic acid as by-product, an improved overall selectivity for products of value without at the same time significantly reducing the catalyst activity.

As a solution for achieving the object of the invention, multimetal oxide compositions comprising Mo, Bi, Fe and Cu and having the general stoichiometry I $$Mo_{12}Bi_aFe_bCu_cCo_dNi_eW_fG_gH_hL_lM_mO_x \quad (I)$$

in which the variables are each defined as follows:
G=one element or more than one element from the group consisting of K, Na, Rb and Cs,
H=one element or more than one element from the group consisting of Ba, Ca, Cr, Ce, La, Mg, Mn, Pb, Sn, Sr and Zn,
L=one element or more than one element from the group consisting of B, Nb, P, Sb, Ta, Te, Ti, Y and Zr,
M=one element or more than one element from the group consisting of Al and Si,
a=0.2 to 2.5,
b=0.5 to 4,
c=0.05 to 0.55,
d+e=4 to 11,
f=0 to 1.2,
g=0.03 to 0.5,
h=0 to 20,
l=0 to 10,
m=0 to 800, and
x=a number which is determined by the valency and frequency of the elements in I other than oxygen,
and fulfill the following conditions:

$$12/(d+e+1.5 \cdot b+h)=0.8 \text{ to } 2, \text{ and}$$

$$a \cdot c=0.01 \text{ to } 1.5$$

were provided.

U.S. Pat. No. 3,951,861 relates to multimetal oxide compositions which comprise Mo, Bi and Fe, must comprise Tl and may optionally also comprise Cu as one of multiple optional elements.

However, a disadvantage of these multimetal oxide compositions that are used in U.S. Pat. No. 3,951,861 likewise as active compositions for the heterogeneously catalyzed partial gas phase oxidation of propene to acrolein as main product and acrylic acid as desired by-product is that thallium is not entirely free of toxicological concern. In the organism, it is always converted to its monovalent form that can cause damage to the nervous system and to the kidneys and liver.

CN-A 102247862 relates to multimetal oxide compositions which comprise Mo, Bi, Ni, Cs and Cu and may also comprise Fe as one of multiple optional elements. They are recommended for active compositions of catalysts wherein the active composition is a composite of multiple layers of different multimetal oxides. The corresponding catalysts are also described as suitable for the catalysis of the heterogeneously catalyzed partial oxidation of propene to the corresponding unsaturated aldehyde.

CN-A 101168129 describes multimetal oxide compositions which comprise Mo, Bi, Ni, Mg, La, Na, Al and Cl and may optionally also comprise Cu as one of multiple optional elements as active compositions suitable for the catalysis of the heterogeneously catalyzed partial ammoxidation of propene to acrylonitrile. A disadvantage of these multimetal oxide compositions is that they must comprise Cl.

CN-A 104646012 relates to multimetal oxide compositions comprising Mo, Bi, Fe, Ni, Co and Cu that are recommended in CN-A 104646012 as active compositions for the heterogeneously catalyzed partial oxidation of propene to acrolein. A disadvantage of these multimetal oxide compositions is that, based on their molar Mo content, they must comprise at least one of the two elements Bi and Cu in comparatively elevated molar amounts, which is not beneficial to the achievement of the object of the invention.

CN-A 102989471 relates to active multimetal oxide compositions comprising Mo, Bi, Fe, Ca, Cs, Si and Cu that are suitable for heterogeneous catalysis of the partial gas phase oxidation of propene to acrolein. A disadvantage of these active compositions is that, based on their molar Mo content, they must comprise both the element Bi and the element Cu in comparatively elevated molar amounts, which is not beneficial to the achievement of the object of the invention.

WO 2010/066645 relates to a process for continuously producing geometric shaped catalyst bodies, the active composition of which is a multielement oxide comprising the element Mo, the elements Bi and/or V and one or more of the elements Co, Ni, Fe, Cu and alkali metals.

Advantageously in accordance with the invention, the stoichiometric coefficient c is 0.05 to 0.5, preferably 0.05 to 0.45, more advantageously 0.05 to 0.4, particularly advantageously 0.05 to 0.35, better 0.1 to 0.3 and most preferably 0.15 to 0.25 or 0.2.

Preferably in accordance with the invention, the product P=a·c fulfills the condition P=0.03 to 1.3, advantageously P=0.05 to 1, particularly advantageously P=0.075 to 0.75, very particularly advantageously P=0.09 to 0.5 and at best P=0.1 to 0.3.

In addition, it is advantageous for the multimetal oxide compositions I of the invention when the quotient $Q^2=d/(d+e)$ fulfills the condition $Q^2=0.45$ to 1, better $Q^2=0.6$ to 1, even better $Q^2=0.7$ to 1, more advantageously $Q^2=0.8$ to 1, particularly advantageously $Q^2=0.9$ to 1 and at best $Q^2=1$ According to the invention, the quotient $Q^1=12/(d+e+1.5 \cdot b+h)$ advantageously fulfills the condition $Q^1=0.9$ to 1.75, preferably $Q^1=0.95$ to 1.5, more preferably $Q^1=1$ to 1.3 and most preferably $Q^1=1$ to 1.2 or 1 to 1.1.

Furthermore, it is favorable in accordance with the invention when the quotient $Q^3=b/(b+d+e+h)$ fulfills the condition $Q^3=0.05$ to 0.4, preferably $Q^3=0.1$ to 0.4, better $Q^3=0.2$ to 0.4, more preferably $Q^3=0.25$ to 0.35 and most preferably $Q^3=0.3$.

Advantageously in accordance with the invention, the stoichiometric coefficient a is 0.5 to 3, particularly advantageously 0.5 to 2, better 0.5 to 1.5, very particularly advantageously 0.5 to 1 or 0.5 to 0.75, and even better 0.6.

Advantageously in accordance with the invention, the stoichiometric coefficient b is 0.5 to 3.5, preferably 1 to 3.5, particularly advantageously 1.5 to 3.5 and very particularly advantageously 1.5 to 3 or 2 to 3.

Advantageously in accordance with the invention, the sum of d+e is advantageously 5 to 11, better 6 to 10, particularly advantageously 6.5 to 9.5 and very particularly advantageously 7 to 9.

Preferably in accordance with the invention, the stoichiometric coefficient g is 0.04 to 0.4, advantageously 0.04 to 0.3, particularly advantageously 0.04 to 0.25 and very particularly advantageously 0.05 to 0.15 or 0.06 to 0.13 or 0.08.

Preferably in accordance with the invention, the stoichiometric coefficient h is 0 to 15, more preferably 0 to 10, advantageously 0 to 5 and very particularly advantageously 0 to 2.5.

Advantageously in accordance with the invention, the stoichiometric coefficient I is 0 to 8, particularly advantageously 0 to 6, better 0 to 4 and even better 0 to 2.

The stoichiometric coefficient m is advantageously 0.1 to 500, preferably 0.2 to 100, more preferably 0.3 to 50, better 0.4 to 30, even better 0.5 to 20, very particularly advantageously 0.6 to 10 or 0.7 to 7 and at best 0.8 to 5 or 1 to 3.6.

In addition, the variable G advantageously means one or more than one element from the group consisting of Cs, K and Na, or of K and Na. More preferably, the variable G has the meaning of K.

Advantageously in accordance with the invention, the variable M means Si.

Preferably in accordance with the invention, the variable H means one or more than one element from the group consisting of Ca, Ce, Mg, Mn, Sn, Sr and Zn, and most preferably one or more than one element from the group consisting of Ce, Mg, Mn and Zn.

Advantageously in accordance with the invention, the variable L means one or more than one element from the group consisting of Nb, P, Sb, Te and Zr, and most preferably one or more than one element from the group consisting of P, Ti and Zr.

BRIEF DESCRIPTION OF THE SEVERAL VIEWS OF THE DRAWINGS

The FIGURE shows a plot of the results shown in table 1 for the inventive shaped unsupported catalyst bodies (□) E1 to E8 and for the comparative shaped unsupported catalyst bodies (●) C1 to C31.

Inventive multimetal oxide compositions of the general stoichiometry I are typically used for catalysis of the respective heterogeneously catalyzed gas phase partial oxidation (especially that of propene to acrolein) having been shaped in neat form (as what are called unsupported catalysts) to give geometric shaped bodies, or else in the form of eggshell catalysts, i.e. preshaped inert (shaped) support bodies coated with the respective (active) multimetal oxide composition I. In principle, the desired geometry of the unsupported catalysts or shaped support bodies is not subject to any restriction in accordance with the invention. This means that the corresponding geometric shaped bodies may have either a regular or irregular shape, preference being given in accordance with the invention to regular-shaped bodies, for example spheres (hollow cylinders) or (solid) cylinders both in the case of the unsupported catalysts and in the case of the shaped support bodies. It will be appreciated that inventive multimetal oxide compositions of the general stoichiometry I can alternatively be used in powder form as catalysts for such catalysis.

In principle, multimetal (oxide) active compositions of the general stoichiometry I can be produced in a simple manner by using suitable sources of their elemental constituents (especially other than oxygen) to produce a very intimate, preferably finely divided, dry mixture of corresponding composition to the respective stoichiometry of the multimetal oxide (active) composition I to be produced, and, optionally after shaping to shaped bodies of regular or irregular geometry, which is optionally effected with additional use of shaping auxiliaries, calcining it at temperatures of 350 to 650° C. The calcination can be effected either under inert gas or under an oxidative atmosphere, for example air (or another mixture of inert gas and molecular oxygen that may also comprise reducing constituents in comparatively small proportions) or else under a reducing atmosphere (for example a mixture of inert gas, $NH_3$, $CO$ and/or $H_2$ that may also comprise oxidizing constituents in comparatively small proportions), or under reduced pressure. The calcination time may be a few minutes to a few hours and is typically shorter at elevated calcination temperature.

Useful sources for the elemental constituents of the inventive multimetal oxide (active) compositions of the general stoichiometry I (i.e. as starting compounds that comprise at least one elemental constituent (at least one element present in the multimetal oxide (active) composition I) in chemically bound form) include those compounds that are already oxides (generally in the solid state of matter under standard conditions (1 atm, 0° C.) (for example metal oxides) and/or those compounds that are convertible to oxides (which are generally in the solid state of matter under standard conditions) by heating (thermal treatment at elevated temperature) at least in the presence of gaseous oxygen and/or of components that release gaseous (for example molecular) oxygen. In principle, the oxygen source may, for example, be in the form of a peroxide constituent of the mixture to be calcined. It is quite generally the case that one starting compound may be the source for more than one elemental constituent of the inventive multimetal oxide composition I.

As well as the oxides, useful starting compounds (sources) of this kind include, in particular, halides, nitrates, formates, acetates, oxalates, citrates, carbonates, amine complexes, ammonium salts and/or hydroxides and hydrates of the aforementioned salts.

Compounds such as $NH_4OH$, $(NH_4)_2CO_3$, $NH_4NO_3$, $NH_4CHO_2$, $CH_3COOH$, $NH_4CH_3CO_2$ and/or ammonium oxalate that break down and/or decompose in the later calcining or earlier essentially completely to give compounds that escape in gaseous form (for example ammonia, $CO_2$, $CO$, $H_2O$, nitrogen oxides) can additionally be incorporated into the intimate dry mixture as what are called pore formers. Useful substances of this kind that break down in the calcining operation also include organic materials, for example stearic acid, malonic acid, ammonium salts of the aforementioned acids, starches (for example potato starch, corn starch), ground nutshells and finely divided ground polymer (for example polyethylene, polypropylene etc.).

There is normally also formation (release) of pore-forming gaseous compounds in the course of the thermal treatment (calcining) outlined when the element sources with which the very intimate and preferably finely divided dry mixture is produced are partly organic in nature (for example in the case of acetates, formates, oxalates and/or citrates) or comprise hydroxide ions, carbonate ions, hydrogencarbonate ions, ammonium ions, halide ions, hydrogenphosphate ions and/or nitrate ions that normally break down in the calcining operation.

The intimate mixing of the starting compounds (sources) for production of multimetal oxide (active) compositions I can be effected in dry or wet form. If it is effected in dry form, the starting compounds (the sources) are appropriately used in the form of fine powders and, after the mixing and optional compaction to give the geometric shaped precursor body, subjected to the calcination.

Preferably in accordance with the invention, however, the intimate mixing of the (element) sources is effected in wet form.

Advantageously in accordance with the invention, therefore, the starting compounds in the form of solutions and/or suspensions are mixed with one another, and the resulting wet (preferably aqueous) mixture M is then dried to give the intimate dry mixture. The solvent and/or suspension medium used is preferably water or an aqueous solution, resulting in an aqueous mixture M as wet mixture M.

Very particularly intimate dry mixtures are obtained in the mixing process described above when the starting materials are exclusively sources of the elemental constituents in dissolved form and/or in colloidally dissolved form. As already mentioned, a starting compound may be a source for just one or more than one of the elemental constituents. In a corresponding manner, an above-detailed solution or colloidal solution may include just one or else more than one elemental constituent of the relevant multimetal oxide composition I to be produced in dissolved form. The preferred solvent here, as already stated, is water. The drying of the resulting aqueous mixtures is preferably effected by spray drying.

If the present document refers to a solution of a source (starting compound, starting substance) in a solvent (especially water), the term "dissolving" is meant in the sense of a molecular or ionic solution. This means that the largest geometric unit of the dissolved starting substance (source) present in the solution inevitably has "molecular" dimensions, and the solution appears "visually empty".

By contrast, colloidal solutions constitute a link between true (molecular and/or ionic) solutions and suspensions. In these colloidally dispersed systems, there are smaller accumulations of molecules or atoms, but these are not apparent either to the naked eye or by microscope. The colloidal solution has an entirely clear (although often colored) visual appearance, since the particles present therein have only a diameter of 1 to 250 nm (preferably to 150 nm and more preferably to 100 nm).

Owing to their small size, it is not possible to remove the colloidally dissolved particles by conventional filtration. However, they can be separated from their "solvent" by ultrafiltration with membranes of vegetable, animal or synthetic origin (for example parchment, pig's bladder or cellophane). By contrast with the "visually empty" true (molecular and/or ionic) solutions, a light beam cannot pass through a colloidal solution without deflection. The light beam is scattered and deflected by the colloidally dissolved particles. In order to keep colloidal solutions stable and to prevent further particle agglomeration, they frequently comprise added wetting aids and dispersing aids and other additives.

While elements (elemental constituents) other than silicon for an inventive multimetal oxide composition I are preferably introduced by dissolved sources in the form of a solution (more preferably in an aqueous solution) for production of the wet (preferably aqueous) mixture M, the element silicon is preferably introduced in the form of a silica sol for production of the wet (preferably aqueous) mixture M.

Silica sols are aqueous colloidal solutions of virtually spherical polysilicic acid particles. The diameter of the particles is in the colloidal range and, according to type, is 5 nm to 75 nm. The particles are pore-free. They have a core of $SiO_2$ that has been hydroxylated on its surface. The spherical individual particles are not crosslinked to one another. For reasons of stability, in silica sols, a portion of the hydroxyl groups is normally in alkali metal hydroxide- and/or ammonium hydroxide-neutralized form. This means that some of the counterions in that case are not protons, but alkali metal (for example Na+) ions and/or $NH_4^+$ cations. The $SiO_2$ content of silica sols suitable in accordance with the invention for production of a wet (preferably aqueous) mixture M may, for example, be 30% to 60% of the weight of the silica sol. Silica sols are normally water-fluid and do not comprise any sedimentable constituents. They can often be kept for years without sedimentation.

Si sources particularly suitable in accordance with the invention are the LUDOX® silica sols from Grace GmbH & KG, In der Hollerecke 1, D-67545 Worms. The particles thereof are discrete spherical spheres of silicon dioxide with no internal surface area or detectable crystallinity. The predominant proportion thereof is dispersed in an alkaline medium that reacts with the hydroxylated surface and results in repellent negative charges.

The particle diameters of silica sols suitable in accordance with the invention may be very narrow (essentially monodisperse) or very broad (polydisperse).

A silica sol particularly suitable for the purposes of the invention (for production of a wet (preferably aqueous) mixture M) is the LUDOX TM50 silica sol from Grace. The LUDOX TM50 silica sol has a very substantially monodisperse (d=22 nm) particle diameter distribution. Its pH (1 atm, 25° C.) is 9.0. The alkali metal ion that replaces the portion of the hydroxyl protons is Na+. The $SiO_2$ content of LUDOX TM50 is 50% of the weight of this hydrogel. The specific surface area of the $SiO_2$ particles present in colloidally dissolved form in LUDOX TM50 is 140 $m^2/g$. The bulk density (1 atm, 25° C.) of LUDOX TM50 is 1.40 $g/cm^3$. The titratable alkali metal content of LUDOX TM50 (calculated as $Na_2O$) is 0.21% by weight (based on the weight of the silica sol). The dynamic viscosity of LUDOX TM50 is 40 mPas (1 atm, 25° C.). The content of Cl− (calculated as NaCl) of LUDOX TM50 is 0.03% by weight and the content of $SO_4^{2-}$ of LUDOX TM50 (calculated as $Na_2SO_4$) is 0.08% by weight (based in each case on the weight of LUDOX TM50).

It will be appreciated that it is also possible for at least one element source in molecularly and/or ionically dissolved form and one or more than one other element source in colloidally dissolved form to be present alongside one another in a solution to be used for production of a wet (especially aqueous) mixture M.

A favorable Mo source in the context of the production of inventive multimetal oxide active compositions I is ammonium heptamolybdate tetrahydrate. This is particularly because it has excellent solubility in water. According to Ullmann's Encyclopedia of Industrial Chemistry, Volume 22, 2003, WILEY-VCH, pages 320/321, a solution of ammonium molybdate tetrahydrate in water at 25° C. and 1 atm has a saturation solubility of 30% by weight (calculated as anhydrous salt).

As a result of production, ammonium molybdate tetrahydrate (as a consequence of process parameters not accurately observed in the production thereof) may be contaminated in minor amounts (usually ppm) with water-insoluble isopolymolybdate. If ammonium heptamolybdate tetrahydrate contaminated in this way is dissolved in water, this gives rise to an aqueous solution that has a certain turbidity owing to the small amounts of finely divided isopolymolybdate present in undissolved form. In-house studies by the applicant have shown that even isopolymolybdate-contaminated ammonium molybdate tetrahydrate, the solution of which in water (determined as described in WO 2016/147324 A1) has a turbidity of 20 NTU, or of 50 NTU, or of 70 NTU, or of 100 NTU, or of 150 NTU, or of 200 NTU, or of 250 NTU, or 300 NTU, is suitable for production of inventive multimetal oxide (active) compositions I without any perceptible impairment of the performance thereof when used as active compositions of catalysts for the heterogeneously catalyzed partial gas phase oxidation of propene to acrolein as main product and acrolein as by-product.

Further Mo sources suitable for production of inventive multimetal oxide active compositions I are, for example, ammonium orthomolybdate ($(NH_4)_2MoO_4$), ammonium dimolybdate ($(NH_4)_2Mo_2O_7$), ammonium tetramolybdate dihydrate ($(NH_4)_2Mo_4O_{13} \times 2H_2O$) and ammonium decamolybdate dihydrate ($(NH_4)_4Mo_{10}O_{32} \times 2\ H_2O$). In principle, molybdenum trioxide is also usable.

A preferred source for the elements represented by the variable G in the general stoichiometry I of the multimetal oxide compositions of the invention, in the context of production of inventive multimetal oxide active compositions I, are the hydroxides thereof. In principle, the nitrates of these elements and the hydrates of these nitrates are also useful as such sources. This means that a preferred K source for production of inventive multimetal oxide (active) compositions I is KOH, but $KNO_3$ or the hydrate thereof can also be used in principle as the K source.

Bi sources used for production of inventive multimetal oxide active compositions I are preferably salts of bismuth that have Bi in the form of $Bi^{3+}$. Examples of useful salts of this kind include bismuth(III) oxide, bismuth(III) oxide nitrate (bismuth subnitrate), bismuth(III) halide (for example fluoride, chloride, bromide, iodide) and especially bismuth(III) nitrate pentahydrate. It will be appreciated that, for production of inventive multimetal oxide active compositions I, the Bi source used may also be a solution of elemental Bi in aqueous nitric acid in which the Bi is in the form of $Bi^{3+}$. In the case of the use (preferred in accordance with the invention) of an aqueous solution of $Bi^{3+}$ nitrate or the hydrate thereof as source (such a solution can also be produced by dissolving elemental Bi in aqueous nitric acid) for production of inventive multimetal oxide active compositions I, it is advantageous in accordance with the invention when the pH thereof (1 atm, 25° C.) is low since this counteracts unwanted formation of $Bi^{3+}$-comprising precipitates in the aqueous solution. This pH is preferably ≤1, more preferably ≤0.5. In general, this pH, however, is ≥−2, usually ≥0. Appropriately for application purposes, such an aqueous solution is a nitric acid solution. This means that its low pH is brought about by excess nitric acid (in this case, the molar ratio $(n_{NO3-})/(n_{Bi3+})$ of the molar amount of $NO_3^-$ ($n_{NO3-}$) present in the aqueous solution to the molar amount of $Bi^{3+}$) ($n_{Bi3+}$) present in the aqueous solution is >3).

Fe sources preferred in accordance with the invention for production of inventive multimetal oxide active compositions I are salts of $Fe^{3+}$, among which particular preference is given to the various iron(III) nitrate hydrates (see, for example, DE-A 102007003076). Particular preference is given in accordance with the invention to using iron(III) nitrate nonahydrate as Fe source for the aforementioned purpose. It will be appreciated that it is also possible to use salts of $Fe^{2+}$ in the context of an inventive production of multimetal oxide active compositions I as Fe source.

Advantageously in accordance with the invention, for production of inventive multimetal oxide compositions I, based on the total molar amount of Fe present therein, at least 50 mol %, better at least 75 mol % and preferably at least 95 mol % or 100 mol % is introduced in the form of an Fe source having the Fe in the form of $Fe^{3+}$. It is also possible for this purpose to use Fe sources having both $Fe^{2+}$ and $Fe^{3+}$.

Co sources of good suitability in accordance with the invention for production of Co-comprising inventive multimetal oxide active compositions I are especially the salts thereof that have the Co in the form of $Co^{2+}$ and/or $Co^{3+}$. Examples of these include cobalt(II) nitrate hexahydrate, $Co_3O_4$, CoO, cobalt(II) formate and cobalt(III) nitrate. For the aforementioned purpose, particular preference is given to the first of these sources. It will be appreciated that, for production of inventive multimetal oxide active compositions I, the Co source used may also be a solution of elemental Co in aqueous nitric acid in which the Co is in the form of $Co^{2+}$.

Cu sources of good suitability in accordance with the invention for production of inventive multimetal oxide active compositions I are especially the salts thereof that have the Cu in the form of $Cu^{1+}$ (for example copper(I) hydroxide and copper(I) halides such as CuF, CuBr, CuCl and CuI) and/or $Cu^{2+}$. $Cu^{2+}$ salts are particularly preferred. Particularly preferred $Cu^{2+}$ salts are copper(II) sulfate, copper(II) acetate, copper(II) oxalate, copper(II) nitrate, copper (II) carbonate, copper(II) formate, copper(II) hydroxide, copper(II) molybdate and the respective hydrates of these salts. Very particular preference is given to using hydrates of copper(II) nitrate (for example the trihydrate thereof or the hemi(pentahydrate) thereof) as Cu sources for production of inventive multimetal oxide active compositions I. It will be appreciated that, for production of inventive multimetal oxide active compositions I, the Cu source used may also be a solution of elemental Cu in aqueous nitric acid in which the Cu is in the form of $Cu^{2+}$. Such a solution may have an excess of nitric acid ($HNO_3$) relative to the stoichiometry "$Cu(NO_3)_2$". Normally, however, the pH (25° C., 1 atm) of such an aqueous solution is not less than 0 (≥0).

In the case of the elemental constituent Ni, preference is given to using $Ni^{2+}$ salts for production of inventive Ni-comprising multimetal oxide (active) compositions I. These especially include nickel(II) carbonate, nickel(II) sulfate, nickel(II) oxide, nickel(II) acetate, nickel(II) formate, nickel (II) hydroxide, nickel(II) oxalate and nickel(II) nitrate and the respective hydrates of these salts. Very particular preference is given to using hydrates of nickel(II) nitrate (for example the hexahydrate thereof) as Ni sources for production of inventive multimetal oxide active compositions I.

For production of inventive multimetal oxide compositions I that comprise W, the tungsten source used with preference is ammonium paratungstate and the hydrates thereof (for example heptahydrate). If the multimetal oxide composition I comprises aluminum, the preferred Al source used for production thereof is Al(III) nitrate and/or hydrates thereof (for example the nonahydrate).

To improve the solubility of, for example, salts of Fe, Co, Cu and/or Ni in an aqueous medium, in the context of the production of inventive multimetal oxide active compositions I, ammonia (or else the aqueous solution thereof) and/or nitric acid (especially as the aqueous solution thereof) may be added to the respective solution if required.

In principle, the production of a wet (for example aqueous) mixture M can be effected under a wide variety of different gas atmospheres (for example under air, argon, nitrogen, steam and/or carbon dioxide). Preferably in accordance with the invention, the production of a wet (for example aqueous) mixture M is effected under air (advantageously, the aqueous mixture M is saturated in air). This is especially true when the cobalt and ion sources used are salts of $Co^{2+}$ and salts of $Fe^{2+}$. This is particularly true when these salts are nitrates and/or hydrates thereof.

As already mentioned, the wet mixture M, preferably in accordance with the invention, is an aqueous mixture M which is particularly advantageously produced in the manner which follows.

If the multimetal oxide composition I does not comprise any element which is represented by one of the variables H and L, the procedure is preferably as follows. At least one source of the element Fe, at least one source of the element Bi, at least one source of the element Cu, at least one source of at least one of the elements Co and Ni and, if the multimetal oxide composition I comprises the element Al, at least one source of the element Al are used to produce an aqueous solution A having a pH of ≤3, preferably ≤2, more preferably ≤1 and most preferably ≤0 (pH values of aqueous solutions relate generally in this document (unless explicitly stated otherwise) to a measurement with a glass electrode in the form of a combination electrode at 1 atm and at the temperature at which the respective aqueous solution is produced; the calibration of the combination electrode required for this purpose is effected under the same conditions by means of aqueous buffer solutions that have a known pH under these conditions which is close to the measurement sought; the Mettler Toledo Inpro 4260/425/Pt 100 pH electrode is especially suitable for determining such pH values, this being a combination electrode with integrated Pt 100 temperature sensor for automatic temperature compensation). In general, the pH of the aqueous solution A is not less than −2 and is particularly advantageously in the range of −1 to 0. Preferably, the aqueous solution A is an aqueous solution of the nitrates or nitrate hydrates of the aforementioned elements. More preferably, the aqueous solution A is an aqueous solution of these nitrates or nitrate hydrates in aqueous nitric acid. Particularly for production of such a solution, suitable element sources are also solutions of the relevant elements in aqueous nitric acid.

At least one source of the element Mo and one or more sources of at least one of the elements which are represented by the variable G are used to produce an aqueous solution B. Advantageously in accordance with the invention, the pH of the aqueous solution B (at 1 atm and that temperature at which solution B is produced) is <7. More preferably, the pH of the aqueous solution B is ≤6.5 and very particularly advantageously ≤6. In general, the pH of the aqueous solution B will be ≥3. Favorable solutions B for use in accordance with the invention have a pH of 4 to 6. Preferably in accordance with the invention, for preparation of the aqueous solution B, the source used for an element which is represented by the variable G is the element hydroxide thereof (for example KOH). A preferred Mo source for preparation of an aqueous solution B is ammonium heptamolybdate tetrahydrate (($NH_4)_6Mo_7O_{24} \times 4H_2O$), which is entirely soluble in water at 25° C. (1 atm) up to saturation solubility (30% by weight, calculated in anhydrous form).

Appropriately in accordance with the invention, the total content in the aqueous solution A of the metal constituents Bi, Fe, Cu etc., based on the total content of the aqueous solution A, is 5% to 20% by weight, advantageously 10% to 15% by weight.

Appropriately in accordance with the invention, the total content in the aqueous solution B of Mo, based on the total amount of the aqueous solution B, is 2% to 25% by weight, advantageously 3% to 20% by weight and particularly advantageously 5% to 15% by weight.

Subsequently, the aqueous solution A and the aqueous solution B are mixed with one another in a manner appropriate for application purposes. Advantageously in accordance with the invention, the procedure here is to stir the aqueous solution A continuously into the aqueous solution B. Advantageously in accordance with the invention, this is done while vigorously stirring the initially charged aqueous solution B.

Appropriately in accordance with the invention, the total content in the resulting aqueous mixture of aqueous solution A and aqueous solution B of the metal constituents Bi, Fe, Cu, Mo etc., based on the total content of the aqueous mixture, is 3% to 20% by weight, advantageously 5% to 15% by weight.

Advantageously in accordance with the invention (preferably over the entire mixing operation), the temperature of the initially charged aqueous solution B and of the vigorously stirred aqueous mixture that results on stirring of the aqueous solution A into it, just like the temperature of the aqueous solution A itself, is $\leq 80°$ C. and $\geq 0°$ C.

Preferably, the aforementioned temperatures are $\leq 75°$ C. and $\geq 30°$ C., and they are more preferably $\leq 70°$ C. and $\geq 50°$ C. or $\leq 65°$ C. and $\geq 55°$ C.

Advantageously, the aqueous solutions A and B and the aqueous mixture that results on stirring of the aqueous solution A into the aqueous solution B have the same temperature. This temperature is at best 60° C. Preferably, the temperatures of the aqueous solution A, the aqueous solution B and the aqueous mixture that results from these are kept constant over the course of the stirring-in process described. For this purpose, for example, thermostat control is possible with the aid of a water bath. The working pressure on stirring of the aqueous solution A into the aqueous solution B is appropriately 1 atm (1.01 bar).

Preferably, the aqueous solution A is stirred into the initially charged aqueous solution B within a period within the range from 5 to 60 minutes, more preferably within a period of 10 to 30 minutes and most preferably within a period of 15 to 25 minutes. The resulting aqueous mixture is subsequently, preferably while maintaining the stirring-in temperature, appropriately for application purposes, stirred for a further 5 to 60 minutes, preferably 10 to 30 minutes and particularly advantageously 15 to 25 minutes.

If the multimetal oxide composition I additionally comprises one or more than one element which is represented by one of the variables H and L, advantageously in accordance with the invention, the procedure is as described above in a corresponding manner, but with the difference that at least one source of the respective additional element is additionally dissolved in at least one of the aqueous solutions A, B produced as described. With the aid of a corresponding dissolution test, it is possible to ascertain readily which of the two aqueous solutions A, B is better suited to the purpose, or if, as the case may be, both of the aqueous solutions A, B are options. If available, preference is given in accordance with the invention to using a nitrate and/or nitrate hydrate in each case of the respective additional element as such a source. If such dissolving of a source in at least one of the two aqueous solutions A, B should not be possible, this additional source may also be suspended in at least one of the two solutions A, B (preferably in very finely divided form). Preferably in accordance with the invention, in this case, the corresponding additional source, however, is suspended in the aqueous mixture produced from the two aqueous solutions A, B (preferably in very finely divided form).

Essentially, the length of the period during which the aqueous solution A and the aqueous solution B are combined has no effect on the selectivity of the multimetal oxide active composition produced later on. However, excessive further stirring ($\geq 4$ h) reduces the selectivity. It has also been found that the length of the aforementioned periods exerts a certain effect on the activity of the multimetal oxide active composition I produced later on. For instance, gradual stirring of the aqueous solution A into the aqueous solution B is beneficial for activity, whereas excessively rapid stirring of the aqueous solution A into the aqueous solution B reduces activity. The latter is also true of excessive further stirring (for example $\geq 3$ h or $\geq 4$ h).

Advantageously in accordance with the invention, the ratio V formed from the total molar amount $n_1$ of $NH_3$ and $NH^{4+}$ optionally present in the aqueous mixture of the aqueous solution A and the aqueous solution B and the total molar amount $n_2$ of Mo present in the same aqueous mixture ($V=n_1 : n_2$) is adjusted such that $V \leq 1.5$, preferably $\leq 1$ and more preferably $\leq 6/7$. In principle, V may also be 0. The pH of the aqueous mixture of the aqueous solution A and the aqueous solution B is advantageously $\leq 3$, better $\leq 2$. In general, it is at values of $\geq 0$.

If the desired inventive multimetal oxide composition I is the elemental constituent Si, preferably in accordance with the invention, aqueous silica sol as the source thereof is stirred into the aqueous mixture of aqueous solution A and aqueous solution B, in which case water may advantageously have been added to this aqueous mixture prior to this stirring-in. In an appropriate manner, both the aqueous silica sol and the water may be added all at once. Both the temperature of the water and the temperature of the aqueous silica sol corresponds advantageously to the temperature of the aqueous mixture of the aqueous solution A and the aqueous solution B. Finally, in an appropriate manner, stirring is continued for up to 30 minutes. During the further stirring, the aforementioned temperature is advantageously maintained. The $SiO_2$ content of the added aqueous silica sol may be 15% to 60% by weight, or 20% to 60% by weight, or 30% to 60% by weight, preferably 40% to 60% by weight and more preferably 45% by weight to 55% by weight (based in each case on the total weight thereof).

Rather than initially charging the aqueous solution B in a thermostatted stirred vessel and then feeding the aqueous solution A into it while stirring, it is also possible to supply both the aqueous solution B and the aqueous solution A continuously to the stirred vessel (for example by means of a "3-way T mixer"). In principle, the aqueous solution B can also be stirred continuously into an initially charged aqueous solution A. However, this procedure is less preferred in accordance with the invention.

In general, the aqueous mixture M obtainable as described is an aqueous suspension (preferably, the ratios V described as advantageous likewise exist in the aqueous mixture M (total molar amount of $NH_3+NH^{4+}$ present to molar amount of Mo present); in addition, the pH of the aqueous mixture M obtainable as described is also advantageously $\leq 3$, generally 0 to 2). Advantageously in accordance with the invention, aqueous mixtures M obtainable as described comprise not more or less than 60 mol % of the total molar amount of Co and/or Ni present therein in a form dissolved in the aqueous medium (at that temperature and the working pressure at which the aqueous mixture M was produced). Preferably, the above-detailed proportion AT of the molar amount of Co and/or Ni present in the aqueous mixture M which is dissolved in the aqueous medium of the aqueous mixture M is at values of ≤50 mol % and more preferably at values of ≤40 mol %, or ≤30 mol % or ≤20 mol %. Appropriately in accordance with the invention, the total content in the aqueous mixture M to be dried (preferably spray-dried) of Bi, Fe, Cu, Mo etc., based on the amount of the aqueous mixture M, is 3% to 20% by weight, advantageously 5% to 15% by weight. In general, AT is ≥10 mol %, or ≥15 mol %.

Preferably in accordance with the invention, the aqueous mixture M is converted to a finely divided intimate dry mixture by spray-drying the aqueous mixture M (the aqueous mixture M is preferably dried as soon as possible after its production). This means that the aqueous mixture M is first divided (sprayed) into fine droplets in a spray drier and these are subsequently dried in the spray drier. Preferably in accordance with the invention, the spray drying is effected in a hot air stream. In principle, for the aforementioned spray drying, it is alternatively possible to use other hot gases (for example nitrogen or nitrogen-diluted air and other inert gases).

The spray drying can be effected either in cocurrent or in countercurrent of the droplets relative to the hot gas. Typical gas inlet temperatures are in the range from 250 to 450° C., preferably 270 to 370° C. Typical gas outlet temperatures are in the range from 100 to 160° C. The spray drying is preferably effected in cocurrent flow of the droplets relative to the hot gas.

The average particle diameter of the resulting spray powder is typically 10 to 100 μm, preferably 15 to 60 μm and more preferably 25 to 50 μm (the diameter is determined to ISO 13320 by means of light scattering on spray powder dispersed in water at 25° C. (0.1 g of spray powder is introduced into 100 g of water and dispersed therein with an ultrasound homogenizer (model: Hydro-2000G, from Malvern Instruments Ltd, 1020602 in England) for 10 minutes (between 1st and 2nd))). In general, references to a standard in this document relate in each case to that version of the standard that was in force at the priority date of this patent application and has a release date (issue date) that has the smallest time difference from the priority date of this patent application.

The tapped bulk density (25° C., 1 atm) of the spray powder is typically 500 to 1300 g/L and preferably 700 to 1100 g/L.

The ignition loss of the spray powder (calcine at 600° C. (powder temperature) under stationary air (present in excess) for 3 h) is typically 20% to 40% by weight, preferably 25% to 35% by weight, of its starting weight.

Until further processing thereof, the spray powder can be intermediately stored in preferably airtight containers (for example drums manufactured from plastic). The storage temperature should not exceed 70° C. and is preferably ≤50° C. In general, the storage temperature will not go below 10° C. Since the spray powder is generally hygroscopic, extended contact thereof with moist air should be avoided. Contact with moist air can impair the handling properties of the spray powder (for example the flowability thereof) and ultimately reduce the catalytic performance of the active multimetal oxide I produced therewith.

It will be appreciated that the aqueous mixture M can also be dried by conventional evaporation (preferably under reduced pressure); the drying temperature will generally not exceed 150° C.). In principle, the drying of an aqueous mixture M can also be effected by freeze drying.

In principle, the dried aqueous mixture M can be calcined as such to give an inventive multimetal oxide (active) composition of the general stoichiometry I. Especially when the aqueous mixture M has been dried by spray drying, however, the resulting spray powder is frequently too finely divided for direct calcination. In this case, the spray powder can first be coarsened prior to a calcination, for example by subsequent compaction. If the compaction is effected in dry form, prior to the compaction, finely divided graphite and/or other shaping auxiliaries mentioned in this document (for example lubricants and/or reinforcers), for example, can be mixed into the spray powder (for example with a drum hoop mixer). For example, the compaction can be conducted with a calender having two counter-rotatory steel rolls. Subsequently, the compactate can be comminuted specifically to the particle size appropriate for the further use contemplated. The simplest way of doing this is, for example, to force the compactate through a sieve with defined mesh size.

In principle, the compaction can alternatively be effected in moist form. For example, the spray powder can be kneaded with addition of water. After the kneading, the kneaded composition can be comminuted back to the desired fineness matched to the subsequent use (cf., for example, DE-A 10049873) and dried.

The finely divided precursor materials obtainable as described can then be calcined as such, and the multimetal oxide (active) composition I powder obtainable can be used as such for catalysis of heterogeneously catalyzed partial gas phase oxidations of, for example, propene to acrolein (for example in a moving bed or fluidized bed reactor). Alternatively, the multimetal oxide (active) composition I powder obtained can also first be shaped to shaped bodies of regular or irregular geometry, and the resulting shaped bodies can be used as catalysts for the heterogeneously catalyzed partial gas phase oxidation of, for example, propene to acrolein (for example in a thermoplate reactor or a fixed bed shell and tube reactor) (cf., for example, DE-A 10063162).

For example, the powder form of the active composition, by compaction to the desired catalyst geometry (for example by tableting, extruding or strand pressing), can be used to produce unsupported catalysts, in which case it is optionally possible prior to and/or during the shaping to add auxiliaries, for example graphite or stearic acid as lubricants and/or shaping auxiliaries and reinforcers such as microfibers of glass, asbestos, silicon carbide or potassium titanate. Suitable unsupported catalyst geometries are, for example, solid cylinders or hollow cylinders having an external diameter and length of 2 to 10 mm or of 2 to 8 mm. The unsupported catalyst may of course also have spherical geometry, in which case the sphere diameter may be 2 to 10 mm or 2 to 8 mm.

It will be appreciated that the pulverulent active composition may also be shaped by applying it to the outer surface of preshaped inert catalyst supports (inert with regard to the partial oxidation catalyzed by the catalysts at a later juncture). The coating of the shaped support bodies for production of such eggshell catalysts can be executed, for example, in a suitable rotatable vessel as known from DE-A 10063162, DE-A 2909671, EP-A 293859, EP-A 714700 and DE-A 4442346.

As an alternative for application purposes, shaped eggshell catalyst bodies can be produced by also undertaking the coating of the shaped support bodies with the uncalcined precursor powder itself and only undertaking calcination on completion of application and optional drying (cf., for example, DE-A 10049873).

The shaped support bodies for use for production of eggshell catalysts are preferably chemically inert, meaning that they essentially do not intervene in the procedure of the partial gas phase oxidation of propene to acrolein, for example, that is to be catalyzed. Useful materials for the shaped support bodies in accordance with the invention are especially aluminum oxide, silicon dioxide, silicates such as clay, kaolin, steatite, pumice, aluminum silicate and magnesium silicate, silicon carbide, zirconium dioxide and thorium dioxide (especially C220 steatite from CeramTec).

The surface of the shaped support body may be either smooth or rough. Advantageously, the surface of the shaped support body is rough since elevated surface roughness generally results in elevated bond strength of the applied shell of finely divided oxidic active composition or of finely divided precursor composition. Frequently, the surface roughness $R_z$ of the shaped support body is in the range from 40 to 200 µm, often in the range from 40 to 100 µm (determined to DIN 4768 Sheet 1 with a "Hommel tester for DIN-ISO surface measures" from Hommelwerke, Germany). In addition, the support material may be porous or nonporous. Appropriately, the support material is nonporous (the total volume of the pores based on the volume of the shaped support body is advantageously 1% by volume).

The fineness of the finely divided composition to be applied to the surface of the shaped support body is of course matched to the desired eggshell thickness. Suitable compositions for the eggshell thickness range from 100 to 500 µm are, for example, finely divided compositions of which at least 50% of the powder particles pass through a sieve of mesh size 1 to 10 µm, wherein the proportion of particles having a longest extent (=longest direct line connecting two points on the surface of a particle) above 50 µm is less than 1% (based on the total number of particles). In general, the distribution of the longest dimensions of the powder particles, as a result of the preparation, corresponds to a Gaussian distribution.

Appropriately, for coating of the shaped support bodies, the surface thereof and/or the finely divided powder composition to be applied is moistened with a liquid binder (for example water or organic solvents such as glycerol or a mixture thereof) and the shaped eggshell body, on completion of application, is dried again, for example by means of hot air. The layer thickness of the finely divided powder composition applied to the shaped support body is appropriately chosen within the range of 10 to 1000 µm, preferably within the range of 100 to 700 µm and more preferably within the range of 300 to 500 µm. Possible eggshell thicknesses are also 10 to 500 µm or 200 to 300 µm.

The shaped support bodies themselves, as already mentioned, may be regularly or irregularly shaped, preference being given to regular-shaped support bodies, for example spheres, solid cylinders or hollow cylinders. It is suitable in accordance with the invention to use, for example, spherical shaped support bodies having a diameter of 1 to 8 mm, preferably 4 to 5 mm. It is alternatively suitable to use cylinders as shaped support bodies that have a length of 2 to 10 mm and an external diameter of 4 to 10 mm. In the case of rings that are suitable in accordance with the invention as shaped support bodies, the wall thickness is additionally typically 1 to 4 mm. Cylinder dimensions suitable in accordance with the invention are also 3 to 6 mm (length), 4 to 8 mm (external diameter) and, in the case of rings, 1 to 2 mm (wall thickness). It will be appreciated that another useful ring geometry suitable in accordance with the invention is 2 to 4 mm (length), 4 to 8 mm (external diameter) and 1 to 2 mm (wall thickness). Support ring geometries that are prominent in accordance with the invention are, for example, 7 mm×3 mm×1.5 mm (external diameter×length×wall thickness) and 5 mm×3 mm×1.5 mm (external diameter×length×wall thickness). Specifically, drying and/or thermal treatment (calcination) after the application of the eggshell can be conducted as described in DE-A 10063162 and DE-A 10049873.

According to the invention, however, the procedure is particularly advantageously such that finely divided precursor composition (from the finely divided intimate dry mixture of the sources of the elemental constituents), appropriately for application purposes, is used to form shaped bodies of regular or irregular geometry by compaction (compressing or compacting), and they are subsequently converted to shaped unsupported catalyst bodies by thermal treatment (calcination).

Further finely divided shaping auxiliaries that may be added to the finely divided precursor composition before and/or during the shaping are, for example, again lubricants, for example graphite, carbon black, polyethylene glycol, polyacrylic acid, stearic acid, starch, mineral oil, vegetable oil, water, boron trifluoride and/or boron nitride. Also useful as shaping auxiliaries are reinforcers such as microfibers of glass, asbestos, silicon carbide or potassium titanate, which, after the shaping by compaction has ended, have a beneficial effect on the integrity of the compact obtained (of the resulting shaped body). Additional use of lubricants in the context of a corresponding shaping operation is described, for example, in documents DE-A 102007004961, WO 2008/087116, WO 2005/030393, US-A 2005/0131253, WO 2007/017431, DE-A 102007005606 and in DE-A 102008040093.

Preferably in accordance with the invention, exclusively finely divided graphite is used as lubricant. Finely divided graphites that are to be used are especially those which are recommended in documents WO 2005/030393, US-A 2005/0131253, WO 2008/087116 and DE-A 102007005606. This is especially true of those graphites that are used in the examples and comparative examples in these documents. Very particularly preferred graphites are Asbury 3160 and Asbury 4012 from Asbury Graphite Mills, Inc., New Jersey 08802, USA, and Timrex® T44 from Timcal Ltd., 6743 Bodio, Switzerland.

Based on the weight of the finely divided precursor composition to be shaped, it may comprise, based on its total weight, for example, up to 15% by weight of finely divided lubricant (for example graphite). Usually, however, the lubricant content in the finely divided precursor composition to be shaped (in the finely divided intimate dry mixture) is ≤9% by weight, in many cases ≤5% by weight, often ≤4% by weight; this is especially the case when the finely divided lubricant is graphite. In general, the aforementioned added amount is ≥0.5% by weight, usually ≥2.5% by weight.

In general, the finely divided precursor composition optionally comprising shaping auxiliaries (the finely divided intimate dry mixture) is compacted to the desired geometry of the shaped body (of the geometric shaped catalyst precursor body) by the action of external forces (pressure) on the precursor composition. The shaping apparatus to be employed here, or the shaping method to be employed here, is not subject to any restriction.

For example, the compacting shaping can be effected by strand pressing, tableting or extrusion. The finely divided precursor composition (the finely divided intimate dry mixture) used here is preferably dry to the touch. However, it may comprise, for example, up to 10% of its total weight of added substances that are liquid under standard conditions (25° C., 1 atm (1.01 bar)). The finely divided precursor composition (the finely divided intimate dry mixture) may also comprise solid solvates (e.g. hydrates) that include such liquid substances in chemically and/or physically bound form. It will be appreciated that the finely divided precursor composition may also be entirely free of such substances.

A shaping process preferred in accordance with the invention by compaction of the finely divided precursor composition (of the finely divided intimate dry mixture) is tableting. The principles of tableting are described, for example, in "Die Tablette", Handbuch der Entwicklung, Herstellung and Qualitätssicherung ["The Tablet", Handbook of Development, Production and Quality Assurance], W. A. Ritschel and A. Bauer-Brandl, 2nd edition, Edition Verlag Aulendorf, and are applicable in an entirely corresponding manner to a tableting process of the invention.

Advantageously, a tableting operation of the invention is conducted as described in documents WO 2005/030393, DE-A 102008040093, DE-A 102008040094 and WO 2007/017431. The ambient temperature around the tableting machine is normally 25° C. Appropriately for application purposes, the particle diameters of the precursor composition to be compacted (of the finely divided intimate dry mixture), optionally as a result of prior coarsening by compaction, are in the range of 100 to 2000 μm, preferably 150 to 1500 μm, more preferably 400 to 1250 μm, or 400 to 1000 μm, or 400 to 800 μm (shaping auxiliary mixed in prior to the compaction is not taken into account here).

Just like the shaping apparatus to be used for compaction or the shaping method to be employed here, the desired geometry of the resulting shaped bodies in the process of the invention is not subject to any restriction either. This means that the shaped catalyst precursor bodies produced in the compacting operation may have either a regular or irregular shape, preference generally being given in accordance with the invention to regular-shaped bodies.

For example, the shaped catalyst precursor body may have spherical geometry. The sphere diameter here may, for example, be 2 to 10 mm, or 4 to 8 mm. The geometry of the shaped catalyst precursor body may alternatively be solid cylindrical or hollow cylindrical (annular).

In both cases, external diameter and height (length) may, for example, be 2 to 10 mm, or 2 to 8 mm, or 3 to 8 mm.

In the case of hollow cylinders (rings), a wall thickness of 1 to 3 mm is generally appropriate. A ring geometry preferred in accordance with the invention (the geometry of an uncalcined green body and of the unsupported catalyst that arises therefrom through calcination are normally essentially the same) is the geometry of 5 mm×5 mm×2 mm (external diameter×height (length)×internal diameter). This is because fixed catalyst beds composed of rings of this geometry result in a particularly small pressure drop for the reaction gas mixture flowing through the fixed catalyst bed (especially in reaction tubes with an internal diameter of 22 mm to 26 mm). A small pressure drop is advantageous especially when the partial oxidation catalyzed by the fixed catalyst bed is being operated at a high space velocity of reaction gas mixture on the fixed catalyst bed (at a high flow rate of the reaction gas mixture flowing through the fixed catalyst bed). Another ring geometry preferred in accordance with the invention (it especially has advantageous bulk characteristics in reaction tubes with relatively small internal diameter (for example 20 mm)) is the geometry 5 mm×3 mm×2 mm (external diameter×height (length)×internal diameter). It will be appreciated that catalyst precursor geometries used may alternatively be all those geometries that are disclosed and recommended in WO 02/062737 and WO 2015/067656. In the case of solid cylinders, the external diameter may also be 1 to 10 mm.

Advantageously in accordance with the invention, the shaping pressures employed in a compaction of finely divided precursor composition (finely divided intimate dry mixture) to be conducted as described are 50 kg/cm² to 5000 kg/cm². Preferably, the shaping pressures are 200 to 3500 kg/cm², more preferably 600 to 2500 kg/cm².

Especially in the case of annular shaped precursor bodies (irrespective of their shape, shaped precursor bodies are also referred to in the literature as green bodies), the shaping compaction of the invention, advantageously in accordance with the invention, is to be conducted such that the side crushing strength SD of the resulting shaped body (cf. DE-A 102008040093, DE-A 102008040094 and WO 2005/030393) satisfies the relation 12 N≤SD≤40 N, preferably 15 N≤SD≤35 N, and more preferably 19 N≤SD≤32 N.

The experimental determination of side crushing strength is conducted as described in documents WO 2005/030393 and WO 2007/017431. It will be appreciated that ringlike green bodies as recommended by DE-A 102008040093 are very particularly preferred in accordance with the invention. The end faces of annular or ringlike shaped bodies, in the described production process for green bodies of the invention, may be either planar (both or just one of the two end faces) or domed (curved) outward (convexly) (cf., in particular, DE-A 102007004961, EP-A 184790, DE-A 102008040093 (for example paragraph [0032] thereof) and DE-A 10200804009 (for example paragraph [0074] thereof) and the embodiments described in individualized form in these documents). In the determination/specification of the height of such geometric shaped bodies, such a convex dome (curvature) is generally not taken into account in the present document. Rings or ringlike shaped bodies with convex (curved) end faces (preferably both end faces have the same curvature) are advantageous in that fixed catalyst beds of annular or ringlike shaped bodies with convex (curved) end face (with otherwise identical geometry) result in a lower pressure drop in the reaction gas mixture flowing through the fixed catalyst bed (in particular in the case of fixed catalyst beds in reaction tubes) than fixed catalyst beds of annular or ringlike shaped bodies with a planar end face. This is true especially when the ring geometry is 5 mm×5 mm×2 mm (external diameter×height (length)×internal diameter). The radius of such a convex curvature is generally 0.4 to 5 times (e.g. 0.8 to 4 times, or 1.2 to 3 times, or 1.6 to 2.6 times) the external diameter of the circular cylinder of the catalyst ring. As already mentioned, a fixed catalyst bed that results in a smaller pressure drop is advantageous especially when the partial oxidation catalyzed by the fixed catalyst bed is being operated at a high space velocity of reaction gas mixture on the fixed catalyst bed (at a high flow rate of the reaction gas mixture flowing through the fixed catalyst bed).

Ring geometries that are particularly advantageous in accordance with the invention for shaped bodies obtainable by compacting finely divided precursor composition (finely divided intimate dry mixture) satisfy the condition Height (length)/External diameter=H/E=0.3 to 1.5 or to 1.2. More preferably, H/E=0.5 to 1.1 or to 1.0. In addition, it is favorable for annular or ringlike green bodies of the invention when the ratio I/E (where I is the Internal diameter of the ring geometry) is 0.3 to 1.5, preferably 0.6 to 1.1.

The aforementioned ring geometries are particularly advantageous when they simultaneously have one of the advantageous H/E ratios and one of the advantageous I/E ratios. Such possible combinations are, for example, H/E=0.3 to 1.5 or to 1.2 and I/E=0.3 to 1.5 or 0.6 to 1.1. Alternatively, H/E may be 0.5 to 1.1 or to 1.0, and I/E may simultaneously be 0.3 to 1.5 or 0.6 to 1.1. In addition, it is favorable for the relevant ring geometries when H is 2 to 7 mm and preferably 2 to 6 mm or 3 to 6 mm. It is also advantageous when E in the rings is 4 to 8 mm, preferably 4 to 6 mm. The wall thickness of green body ring geometries that are preferred in accordance with the invention is 1 to 2 mm or to 1.5 mm.

Possible ring geometries of the invention are thus (E×H× I) 5 mm×5 mm×2 mm, or 5 mm×2 mm×2 mm, or 5 mm×3 mm×2 mm, 5 mm×5 mm×2.5 mm, or 5 mm×3 mm×2.5 mm, or 5.5 mm×5.5 mm×2.5 mm, or 5.5 mm×5.5 mm×3 mm, or 5 mm×3 mm×3 mm, or 5.5 mm×3 mm×3.5 mm, or 6 mm×3 mm×4 mm, or 6 mm×6 mm×3 mm, or 6 mm×6 mm×3.5 mm, or 6.5 mm×3 mm×4.5 mm, or 7 mm×3 mm×5 mm, or 7 mm×7 mm×3 mm, or 7 mm×3 mm×4 mm, or 7 mm×7 mm×4 mm.

It is generally found to be advantageous for the process of the invention for production of multimetal oxide (active) compositions I when each of the sources used for production of the finely divided intimate dry mixtures to be produced from the sources of the elemental constituents of the multimetal oxide composition I other than oxygen, in the course of production of the finely divided intimate dry mixture, goes through a degree of division having the characteristic feature that its diameter $d^S_{90}$ is $\leq 5$ μm.

The requirement $d^S_{90} \leq 5$ μm is basically fulfilled when a Source is dissolved in a solvent (the term "dissolving" is meant here in the sense of a molecular or ionic solution). The reason for this is that, in the dissolving of a source (starting compound) in a solvent, the source is divided molecularly or ionically in the solvent. This means that the largest geometric unit of the dissolved starting substance (source) present in the solution inevitably has "molecular" dimensions that are thus necessarily significantly less than 5 μm (as already stated, a starting compound may be a source for more than one element, and a solution may include more than one dissolved source).

The requirement $d^S_{90} \leq 5$ μm is alternatively fulfilled when a Source of an element is present in a solvent in colloidal solution since the units present "dissolved" therein have only a diameter of 1 to 250 μm, and therefore the corresponding $d^S_{90}$ is necessarily $\leq 5$ nm.

The requirement $d^S_{90} \leq 5$ μm is alternatively fulfilled when a source is comminuted to this particle size, for example in dry form (for example by grinding).

The particle diameter $d^S_{90}$ relates to the particle diameter distribution of the dry powder, which is to be determined as follows.

The finely divided powder is guided through a dispersing channel into the Scirocco 2000 dry disperser (from Malvern Instruments Ltd., Worcestershire WR14 1AT, United Kingdom), where it is dispersed in dry form with compressed air and blown into the measurement cell in a free jet. The Malvern Mastersizer S laser diffraction spectrometer (likewise from Malvern Instruments Ltd.) is then used to determine the volume-based particle diameter distribution therein to ISO 13320.

A particle diameter $d_x$ based on such a particle diameter distribution is defined such that X % of the total particle volume consists of particles having this or a smaller diameter. This means that (100−X) % of the total particle volume consists of particles having a diameter $>d_x$. Unless explicitly mentioned otherwise in this document, particle diameter determinations and $d_x$ taken therefrom, for example $d_{90}$, $d_{50}$ and $d_{10}$, relate to a dispersion pressure of 2 bar absolute employed in the determination (which determines the intensity of the dispersion of the dry powder during the measurement). $d^S_{90}$ is such a particle diameter $d_{90}$ of a pulverulent Source.

All figures given in this document with regard to an x-ray diffractogram relate to an x-ray diffractogram obtained using Cu—K$_\alpha$ radiation as x-radiation (diffractometer Theta-Theta Bruker D8 Advance, tube voltage: 40 kV, tube current: 40 mA, aperture V20 (variable), collimator V20 (variable), detector aperture (0.1 mm), measurement interval (2Θ=2 theta): 0.02°, measurement time per step: 2.4 s, detector: Si semiconductor detector).

All figures in this document for specific surface areas of solids relate to determinations to DIN 66131 (determination of the specific surface area of solids by gas adsorption ($N_2$) according to Brunauer-Emmett-Teller (BET)), unless explicitly stated otherwise.

All figures in this document for total pore volumes and for pore diameter distributions over these total pore volumes relate to determinations by the method of mercury porosimetry employing the Auto Pore V 9600 system (MicroActive Interactive Dara Analysis Software) from Micromeritics GmbH, D-52072 Aachen (range: 0.1-61 000 psi) at 23° C. (evaluation by Washburn equation using a contact angle of mercury of 140° and a surface tension of mercury of 480 mN/m=480 dyn/cm).

Advantageously in accordance with the invention, shaped unsupported catalyst precursor bodies have a minimum residual moisture content. This is especially true when the intimate mixing of the various sources of the elemental constituents of the multimetal oxide composition I other than oxygen was effected in wet form (especially when an aqueous mixture M was formed).

Preferably in accordance with the invention, the residual moisture content of green bodies that are advantageous in accordance with the invention is at values of $\leq 10\%$ by weight, better $\leq 8\%$ by weight, even better $\leq 6\%$ by weight, and at best $\leq 4\%$ by weight or $\leq 2\%$ by weight (residual moisture content can be determined as described in "Die Bibliothek der Technik" [The Library of Technology], volume 229, "Thermogravimetrische Materialfeuchtebestimmung" [Thermogravimetric Determination of Material Moisture Content], Grundlagen and praktische Anwendungen [Basics and Practical Applications], Horst Nagel, verlag moderne industrie (for example with the aid of a Computrac MAX 5000 XL from Arizona Instruments)).

If the green bodies originate from an aqueous mixture M (such that the residual moisture content thereof consists of water), the residual moisture content is determined, appropriately for application purposes, with microwaves (e.g. with the LB 456 microwave system from BERTHOLD TECHNOLOGIES).

In this procedure, the microwave irradiates the material to be examined with very low power (0.1 mW) (the material undergoes essentially no change in temperature as a result of the comparatively low power). The material constituents are polarized to different degrees as a result. In reaction, the microwave loses speed and energy. The influence of water molecules here is significantly greater than the influence of other constituents, which enables the selective determination of residual water contents. This is because water molecules, on account of their size and their dipole capacity, have particularly good ability to following an electromagnetic alternating field in the microwave frequency region by dipole alignment. In so doing, they absorb energy and alter the electromagnetic alternating field with their electrical properties. This field attenuation and field alteration is the basis of the measurement principle. For example, it is possible to build up a weak microwave field across the sensor area of a planar sensor and permanently analyze the resonance frequency of the sensor system by scanning the microwave frequency. If a water-containing measurement material is moved across the sensor, there is a shift in the resonance frequency and attenuation of the amplitudes thereof. There is a rise both in damping and shift in resonance frequency with increasing amount of water, i.e. with increasing bulk density of the measurement material. However, the ratio of shift in frequency and damping is a density-independent measure of the percentage water content and hence the key to the measurement of moisture content. The ratio forms what is called the microwave moisture measurement, which represents the total moisture content. Since the microwave resonance method is an indirect moisture measurement method, calibration is necessary. In such a calibration measurement, the sensor is used to measure material samples with defined moisture content. The relationship of the microwave moisture measurements to the corresponding defined absolute material moisture contents then forms the calibration of the measurement system. Measurement accuracy is typically ±0.1% moisture content (for example, the water moisture content can be determined with a Sartorius PMD300PA online moisture analyzer).

Against this background, spray drying of a wet (e.g. aqueous) mixture M should already be conducted such that the resulting spray powder has a minimum residual moisture content.

Green bodies produced in accordance with the invention, taking account of the aspect just addressed, should be stored as far as possible with exclusion of ambient air (having air humidity) (preferably, storage until calcination is effected under anhydrous inert gas or under predried air or in airtight containers).

Advantageously in accordance with the invention, the forming/shaping and storage of finely divided intimate dry mixture is conducted with exclusion of ambient air (having air humidity) (for example under $N_2$ atmosphere).

The green bodies (or generally finely divided precursor powder or shaped support bodies coated with this precursor powder) are normally calcined at temperatures (calcination temperatures) that reach or generally exceed at least 350° C. Normally, however, the temperature of 650° C. is not exceeded in the course of calcination (the term "calcination temperature" in this document means the temperature present in the calcination material (advantageously in accordance with the invention, the calcination material has a very uniform (homogeneous) calcination temperature; this is correspondingly true of the other calcination conditions)). Advantageously in accordance with the invention, in the course of calcination, the temperature of 600° C., preferably the temperature of 550° C. and frequently the temperature of 530° C. is not exceeded. Moreover, in the course of the above calcination, preferably the temperature of 380° C., advantageously the temperature of 400° C., particularly advantageously the temperature of 420° C. and most preferably the temperature of 440° C. is exceeded. The calcination may also be subdivided into multiple sections over its duration.

Experience has shown that the calcination is advantageously preceded by a thermal treatment at temperatures of ≥120° C. and <350° C., preferably ÷150° C. and ≤320° C., more preferably ≥170° C. and ≤290° C. Appropriately for application purposes, such a thermal treatment is conducted until the constituents that are present within the composition to be subjected to thermal treatment and break down to gaseous compounds under the conditions of the thermal treatment have largely (preferably completely) broken down to give gaseous compounds (the time taken in this regard may, for example, be 3 h to 15 h, frequently 4 h to 10 h or 5 h to 8 h). This is generally the case when, firstly, the molar amount of cations other than metal ions present in the composition which is subsequently to be calcined, based on the total molar amount of cations present, is ≤20 mol % (preferably ≤10 mol %) and, secondly, the molar amount of anions other than $O^{2-}$ present in the same composition, based on the total molar amount of anions present, is likewise ≤20 mol % (preferably ≤10 mol %).

Temperature windows favorable in accordance with the invention for the final calcination temperature are therefore within the temperature range of 400° C. to 600° C., or preferably in the temperature range of 420 to 550° C., or more preferably in the temperature range of 450 to 530° C.

The total calcination time generally extends to more than 0.5 h, and frequently to more than 2 h. Usually, in the calcination, treatment times of 45 h, or of 30 h, are not exceeded. The total calcination time is often below 25 h. In principle, a shorter calcination time is generally sufficient at higher calcination temperatures than at lower calcination temperatures. In one embodiment of the calcination which is advantageous in accordance with the invention, 550° C. is not exceeded, and the calcination time in the temperature window of ≥430° C. and ≤550° C. extends to >4 to ≤25 h.

The overall thermal treatment (including a breakdown phase) of a precursor composition (for example a green body) can be effected either under inert gas or under an oxidative atmosphere, for example air (or another mixture of inert gas and molecular oxygen) and under a reducing atmosphere (for example a mixture of inert gas, $NH_3$, CO and/or $H_2$, or under methane, acrolein, methacrolein). The thermal treatment can of course also be executed under reduced pressure. The atmosphere can also be varied over the course of the thermal treatment.

Preferably in accordance with the invention, the thermal treatment (especially the calcination phase) is effected in an oxidizing atmosphere. Appropriately in application terms, this atmosphere consists predominantly of stationary air or (preferably) of moving air (more preferably, an air stream flows through the composition to be subjected to thermal treatment (the calcination material)). However, the oxidizing atmosphere may likewise consist of a stationary or moving mixture of, for example, 25% by volume of $N_2$ and 75% by volume of air, or 50% by volume of $N_2$ and 50% by volume of air, or 75% by volume of $N_2$ and 25% by volume of air (a treatment atmosphere composed of 100% by volume of $N_2$ is likewise possible).

In principle, the thermal treatment (for example the calcination) of the precursor composition (for example of the green bodies) can be conducted in a wide variety of different oven types, for example heatable air circulation chambers (air circulation ovens, for example air circulation shaft ovens), staged ovens, rotary ovens, belt calciners or shaft ovens. Advantageously in accordance with the invention, the thermal treatment (for example the calcination) is effected in a belt calciner apparatus as recommended by DE-A 10046957 and WO 02/24620. Hotspot formation within the material to be treated (within the calcination material) is very substantially prevented here in that, with the aid of ventilators, elevated volume flow rates of calcination atmosphere are conveyed through the calcination material on a gas-permeable conveyor belt that bears the calcination material (these assure very substantial homogeneity of the calcination temperature in the calcination material).

In the thermal treatment of the precursor compositions to be conducted as described (for example of the green bodies), shaping auxiliaries used can either be preserved in the resulting shaped catalyst body or at least partly escape in gaseous form therefrom as a result of thermal and/or chemical breakdown to give gaseous compounds (e.g. CO, $CO_2$). Shaping auxiliaries remaining in the shaped catalyst body, in the course of a catalytic use thereof, have essentially an exclusively diluting effect on the multielement oxide I active composition. In principle, the thermal treatment in this regard can be effected as described in US 2005/0131253.

Typically, the side crushing strengths of annular shaped unsupported catalyst bodies obtainable as described in accordance with the invention are 5 to 20 N, frequently 6 to 15 N or 6 to 13 N.

Advantageously for application purposes, the specific (BET) surface area of inventive multimetal oxide (active) compositions I (especially when they have been formed, as described above, to annular unsupported catalysts) is 2 to 20 or to 15 $m^2/g$, preferably 3 to 10 $m^2/g$ and more preferably 4 to 8 $m^2/g$. Advantageously in accordance with the invention, the corresponding total pore volume (mercury porosimetry) is in the range from 0.1 to 1 $cm^3/g$ to 0.8 $cm^3/g$, preferably in the range of 0.1 to 0.6 $cm^3/g$ and more preferably in the range of 0.2 to 0.5 $cm^3/g$.

If the pore diameter in μm is plotted on the abscissa and the logarithm of the differential contribution in $cm^3/g$ of the respective pore diameter to the total pore volume in $cm^3/g$ on the ordinate, multimetal oxide (active) compositions I that are particularly favorable in accordance with the invention (especially when they have been formed, as described above, to annular unsupported catalysts) generally show an essentially monomodal distribution (have only one pronounced maximum). If the contribution of pores having a pore radius of ≤0.1 μm to the total pore volume is ≤0.05 $cm^3/g$, the result is particularly good overall target product selectivities (for example in the case of a heterogeneously catalyzed partial oxidation of propene to acrolein and/or acrylic acid). If the contribution of such comparatively narrow pores to the total pore volume is >0.05 $cm^3/g$, an increase in the calcination time and/or the calcination temperature can bring about a reduction in this contribution which is advantageous in accordance with the invention.

Furthermore, for an elevated overall target product selectivity, it is found to be advantageous when the contribution of pores having a pore radius in the range of 0.2 to 0.4 μm to the total pore volume, based on the total pore volume, is >70% by volume, advantageously ≥75% by volume, particularly advantageously ≥85% by volume, preferably ≥90% by volume and more preferably ≥95% by volume or ≥98% by volume.

It will be appreciated that an inventive multimetal oxide (active) composition of the general stoichiometry I can also be used for catalysis of heterogeneously catalyzed partial gas phase oxidations having been diluted with inert materials. Suitable inert diluent materials of this kind include element oxides that have been calcined at high temperatures and hence have a comparatively low level of pores, such as aluminum oxide, silicon dioxide, thorium dioxide and zirconium dioxide. Alternatively, finely divided silicon carbide or finely divided silicates such as magnesium silicate and aluminum silicate or steatite may be used for the aforementioned purpose. Advantageously for application purposes, the procedure here will be, for example, to grind the calcined multimetal oxide (active) composition of the general stoichiometry I to a finely divided powder. Appropriately for application purposes, this is then mixed with finely divided diluent material, and the resulting mixed powder is formed using a shaping method presented in this document (preferably by tableting) to a geometric shaped body. By subsequently calcining once again, the latter is then transformed to the corresponding shaped catalyst body. The finely divided inert diluent material can of course, however, already be incorporated, for example, into a wet (for example aqueous) mixture M prior to the drying thereof. In addition, finely divided inert diluent material can be incorporated into a finely divided dry mixture of sources of the elemental constituents of the multimetal oxide composition I. However, such procedures are less preferred in accordance with the invention.

More particularly, it is a feature of inventive multimetal oxide (active) compositions of the general stoichiometry I produced by the advantageous production processes described (or of shaped unsupported catalyst bodies comprising them) that they have essentially no local sites composed of element oxides (for example bismuth oxide, iron oxide or copper oxide). Instead, these elements are very substantially part of complex mixed oxomolybdates comprising Bi, Fe, Cu and Mo. This is found to be favorable with regard to the inventive aim of minimization of full combustion of organic reaction gas mixture constituents, which is undesirable in accordance with the invention, in the course of the relevant heterogeneously catalyzed partial oxidations.

Otherwise, the procedure for production of unsupported catalysts based on the inventive multimetal oxides I, from the point of view of maximum efficiency of material utilization, appropriately for application purposes, is as in WO 2010/066645.

Inventive multimetal oxide (active) compositions of the general stoichiometry I are suitable as active compositions not just for catalysis of the heterogeneously catalyzed partial oxidation of propene to acrolein but generally for catalysis of heterogeneously catalyzed partial gas phase oxidations of alkanes, alkanols, alkenes and/or alkenals having 3 to 6 carbon atoms (partial oxidations shall be understood in this document especially to mean those conversions of organic compounds with reactive involvement of molecular oxygen in which the organic compound to be partially oxidized, after the reaction has ended, comprises at least one oxygen atom more in chemically bound form than prior to performance of the partial oxidation). The term "partial oxidation" in this document shall alternatively comprise oxidative dehydrogenation and partial ammoxidation, i.e. a partial oxidation in the presence of ammonia.

Inventive multimetal oxide (active) compositions of the general stoichiometry I are particularly suitable for catalysis of the heterogeneously catalyzed partial gas phase oxidation of propene to acrolein, of isobutene to methacrolein, and for catalysis of the heterogeneously catalyzed partial gas phase oxidation of propene to acrylonitrile and of isobutene to methacrylonitrile.

As already mentioned, the heterogeneously catalyzed partial gas phase oxidation of propene (isobutene and/or tert-butanol) to acrolein (methacrolein) forms the first stage of a two-stage heterogeneously catalyzed partial gas phase oxidation of propene (isobutene and/or tert-butanol) to acrylic acid (methacrylic acid), as described by way of example in WO 2006/42459.

Formation of acrylic acid (methacrylic acid) by-product associated with a heterogeneously catalyzed partial gas phase oxidation of propene (isobutene) to acrolein (methacrolein) is therefore generally not undesirable and is normally covered by the desired formation of products of value.

The above is especially true of inventive annular shaped unsupported catalyst bodies comprising multimetal oxide compositions of the general stoichiometry I.

The heterogeneously catalyzed partial oxidation (especially that of propene to acrolein) can be conducted as described, for example, in documents DE-A 102007004961, WO 02/49757, WO 02/24620, DE-A 102008040093, WO 2005/030393, EP-A 575897, WO 2007/082827, WO 2005/113127, WO 2005/047224, WO 2005/042459, WO 2007/017431, DE-A 102008042060, WO 2008/087116, DE-A 102010048405, DE-A 102009047291, DE-A 102008042064, DE-A 102008042061, WO 2015/067656 and DE-A 102008040094 for similar multimetal oxide compositions and catalysts comprising them (more particularly, it is possible here to proceed in a corresponding manner to that in the illustrative embodiments of these documents).

However, catalysts (shaped catalyst bodies) that include multimetal oxide (active) compositions of the general stoichiometry I and are obtainable as described (especially the annular shaped unsupported catalyst bodies (in particular the ring geometries emphasized in individualized form in this document)) are also advantageous when the space velocity of propene, isobutene and/or tert-butanol (or the methyl ether thereof) present in the reaction gas input mixture on the catalyst charge of a reactor is ≥130 L (STP)/L of catalyst charge·h, or ≥140 L (STP)/L·h, or ≥150 L (STP)/L·h, or ≤160 L (STP)/L·h (upstream and/or downstream beds of pure inert material are not considered to form part of the catalyst charge in considerations of space velocity in this document; the volume of the catalyst charge (of the fixed catalyst bed) is incidentally the bed volume thereof within the reactor). Normally, the aforementioned space velocity of the catalyst charge will be ≤600 L (STP)/L·h, frequently ≤500 L (STP)/L·h, in many cases ≤400 L (STP)/L·h or ≥350 L (STP)/L·h. Space velocities in the region of ≥160 L (STP)/L·h or ≥180 L (STP)/L·h to ≤300 or ≤250 or ≤200 L (STP)/L·h are particularly appropriate.

In this document, the space velocity of reaction gas input mixture on a fixed catalyst bed is understood to mean the amount of reaction gas input mixture in standard liters (=L(STP); the volume in liters that the corresponding amount of reaction gas input mixture would occupy under the standard conditions of 0° C. and 1 atm (1.01 bar)) which is supplied to the fixed catalyst bed, based on the volume of its bed (not including bed sections of pure inert material), i.e. on its bed volume, per hour (→unit=L (STP)/L·h). In this document, the units of standard volume such as L (STP) or m³ (STP) always relate (unless explicitly stated otherwise) to the standard conditions of 0° C. and 1 atm (1.01 bar).

The space velocity may also be based only on one constituent of the reaction gas input mixture (for example only on the organic starting compound to be partially oxidized). In that case, it is the volume of this constituent (for example of the organic starting compound of the partial oxidation) which is supplied to the fixed catalyst bed (the catalyst charge of the reactor), based on the volume of its bed, per hour.

It will be appreciated that catalysts obtainable in accordance with the invention (for example annular shaped unsupported catalyst bodies) can also be operated in a manner advantageous in accordance with the invention as catalysts for the partial oxidation of propene to acrolein or of isobutene and/or tert-butanol (or the methyl ether thereof) to methacrolein at space velocities of the starting compound to be partially oxidized on the catalyst charge of ≤130 L (STP)/L·h, or ≤120 L (STP)/L·h, or ≤110 L (STP)/L·h, or ≤100 L (STP)/L·h, or ≤90 L (STP)/L·h. In general, however, this space velocity will be at values of ≥20 L (STP)/L·h, or ≤30 L (STP)/L·h, or ≥40 L (STP)/L·h, or ≥50 L (STP)/L·h, or ≥60 L (STP)/L·h, or ≥70 L (STP)/L·h, or 80 L (STP)/L·h.

In principle, the space velocity of the starting compound to be partially oxidized (propene, isobutene and/or Cert-butanol (or the methyl ether thereof)) on the catalyst charge of a reactor (on a fixed catalyst bed) can be adjusted via two adjusting screws:
  a) the space velocity of reaction gas input mixture (the reaction gas mixture which is supplied to the fixed catalyst bed) on the catalyst charge),
and/or
  b) the content of the starting compound to be partially oxidized in the reaction gas input mixture.

The catalysts obtainable in accordance with the invention (for example annular shaped unsupported catalyst bodies) are also suitable especially when, at space velocities of the organic compound to be partially oxidized on the catalyst charge above 130 L (STP)/L·h, the space velocity is adjusted via the aforementioned adjustment screw a) in particular.

In general, for example, the propene content (isobutene content or tert-butanol content (or the methyl ether content)) in the reaction gas input mixture, essentially irrespective of the space velocity on the catalyst charge, will be 4% to 20% by volume, frequently 5% to 15% by volume, or 5% to 12% by volume, or 5% to 8% by volume (based in each case on the total volume (flow rate) of the reaction gas input mixture flowing toward the fixed catalyst bed).

Frequently, the gas phase partial oxidation process of the partial oxidation catalyzed by catalysts of the invention obtainable as described (for example annular shaped unsupported catalyst bodies or other geometric shaped catalyst bodies) will be conducted (essentially irrespective of the space velocity) at a volume ratio of (organic) compound to be partially oxidized (for example propene):oxygen:inert gases (including steam) in the reaction gas input mixture of 1:(1.0 to 3.0):(5 to 25), preferably 1:(1.5 to 2.3):(10 to 20).

Inert gases are understood here to mean those gases which, in the course of the partial oxidation, in a single pass of the reaction gas mixture through the catalyst bed, remain chemically unchanged to an extent of at least 95 mol %, preferably to an extent of at least 98 mol %.

In the above-described reaction gas input mixtures, the inert gas may consist of molecular nitrogen to an extent of ≥20% by volume, or to an extent of ≥30% by volume, or to an extent of ≥40% by volume, or to an extent of ≥50% by volume, or to an extent of ≥60% by volume, or to an extent of ≥70% by volume, or to an extent of ≥80% by volume, or to an extent of ≥90% by volume, or to an extent of ≥95% by volume.

However, at higher space velocities of the organic compound to be partially oxidized on the catalyst charge of the reactor (for example of ≥150 L (STP)/L·h), the additional use of inert diluent gases having elevated molar heats and/or thermal conductivities, such as propane, ethane, methane, pentane, butane, $CO_2$, CO, steam and/or noble gases is advisable (but not obligatory) for the reaction gas input mixture. In general, these inert gases and mixtures thereof may also be used even at lower space velocities of the organic compound to be partially oxidized on the catalyst charge. Cycle gas can also be used in part as diluent gas. Cycle gas is understood to mean the tail gas that remains when the target compound is separated essentially selectively from the product mixture of the partial oxidation. It should be taken into account here that the partial oxidations to acrolein or methacrolein with the shaped catalyst bodies, for example annular shaped catalyst bodies, obtainable in accordance with the invention may be just the first stage of a two-stage partial oxidation to acrylic acid or methacrylic acid as the actual target compounds, such that the cycle gas is usually formed only after the second stage (typical cycle gas compositions in the case of a heterogeneously catalyzed partial oxidation of propene to acrolein and/or acrylic acid are shown in DE-A 10232482 in paragraphs [0063] and [0075] thereof). In the context of such a two-stage partial oxidation, in general, the product gas mixture from the first stage is fed as such, optionally after cooling and/or secondary oxygen addition (generally in the form of air), to the second partial oxidation stage.

In the partial oxidation of propene to acrolein, using the catalysts of the invention obtainable as described (for example annular shaped catalyst bodies), a typical composition of the reaction gas input mixture measured at the reactor inlet (irrespective of the space velocity chosen) may comprise the following components for example:
  6% to 6.5% by vol. of propene,
  1% to 3.5% by vol. of $H_2O$,
  0.2% to 0.5% by vol. of CO,
  0.6% to 1.2% by vol. of $CO_2$,
  0.015% to 0.04% by vol. of acrolein,
  10.4% to 11.3% by vol. of $O_2$, and
  as the remainder to 100% by vol. molecular nitrogen;
or:
  5.6% by vol. of propene,
  10.2% by vol. of oxygen,
  1.2% by vol. of $CO_x$,
  81.3% by vol. of $N_2$, and
  1.4% by vol. of $H_2O$.

The former compositions are especially suitable at propene space velocities of ≤130 L (STP)/L·h, and the latter composition especially at propene space velocities of <130 L (STP)/L·h, especially ≤100 L (STP)/L·h (for example for startup of the partial oxidation), on the fixed catalyst bed.

Useful alternative compositions of the reaction gas input mixture for an inventive propene partial oxidation to acrolein (irrespective of the space velocity chosen) include those that have the following component contents:
  4% to 25% by vol. of propene,
  6% to 70% by vol. of propane,
  5% to 60% by vol. of $H_2O$,
  8% to 65% by vol. of $O_2$, and
  0.3% to 20% by vol. of $H_2$;
or
  4% to 25% by vol. of propene,
  6% to 70% by vol. of propane,
  0% to 60% by vol. of $H_2O$,
  8% to 16% by vol. of $O_2$,
  0% to 20% by vol. of $H_2$,
  0% to 0.5% by vol. of CO,
  0% to 1.2% by vol. of $CO_2$,
  0% to 0.04% by vol. of acrolein,
  as the remainder to 100% by vol. essentially $N_2$;
or
  50% to 80% by vol. of propane,
  0.1% to 20% by vol. of propene,
  0% to 10% by vol. of $H_2$,
  0% to 20% by vol. of $N_2$,
  5% to 15% by vol. of $H_2O$, and
  sufficient molecular oxygen that the molar ratio of oxygen content to propene content is 1.5 to 2.5;
or
  6% to 9% by vol. of propene,
  8% to 18% by vol. of molecular oxygen,
  6% to 30% by vol. of propane, and
  32% to 72% by vol. of molecular nitrogen.

An alternative composition of the reaction gas input mixture of a heterogeneously catalyzed partial propene partial oxidation with catalysts of the invention to acrolein may be as follows:
  4% to 15% by vol. of propene,
  1.5% to 30% by vol. (frequently 6% to 15% by vol.) of water,
  ≥0% to 10% by vol. (preferably ≥0% to 5% by vol.) of constituents other than propene, water, oxygen and nitrogen, and sufficient molecular oxygen that the molar ratio of molecular oxygen present to molecular propene present is 1.5 to 2.5, and as the remainder up to a total amount of 100% by volume molecular nitrogen.

Another possible reaction gas input mixture composition may comprise:
  6.0% by vol. of propene,
  60% by vol. of air, and
  34% by vol. of $H_2O$.

Alternatively, it is also possible to use reaction gas input mixtures of the composition according to Example 1 of EP-A 990 636, or according to Example 2 of EP-A 990 636, or according to Example 3 of EP-A 1 106 598, or according to Example 26 of EP-A 1 106 598, or according to Example 53 of EP-A 1 106 598 for an inventive propene partial oxidation to acrolein.

The catalysts of the invention obtainable as described, for example annular shaped catalyst bodies, are also suitable for the processes of DE-A 10246119 or DE-A 10245585.

Further reaction gas input mixtures suitable in accordance with the invention may be within the following composition pattern:
  7% to 11% by vol. of propene,
  6% to 12% by vol. of water,
  ≥0% to 5% by vol. of constituents other than propene, water, oxygen and nitrogen,
  sufficient molecular oxygen that the molar ratio of molecular oxygen present to propene present is 1.6 to 2.2, and
  as the remainder up to a total amount of 100% by volume molecular nitrogen.

In the case of methacrolein as target compound, the reaction gas input mixture may especially also be of the composition as described in DE-A 44 07 020.

The reaction temperature for an inventive heterogeneously catalyzed propene partial oxidation to acrolein, in the case of use of the catalysts of the invention obtainable as described (for example annular shaped unsupported catalyst bodies), is frequently 300 to 450° C., or to 400° C., or to 380° C. A reaction temperature window particularly preferred in accordance with the invention is 305 to 345° C. The same is true in the case of methacrolein as target compound.

The reaction pressure for the aforementioned partial oxidations is generally 0.5 to 4 or to 3 bar, or preferably 1.1 or 1.5 to 4 or to 3 bar (what are meant in this document, unless explicitly stated otherwise, are always absolute pressures).

The total space velocity of reaction gas input mixture on the catalyst charge in the aforementioned partial oxidations of the invention typically runs to 1000 to 10 000 L (STP)/ L·h, usually to 1500 to 5000 L (STP)/L·h and often to 2000 to 4000 L (STP)/L·h.

Useful propene for use in the reaction gas input mixture is, in particular, polymer grade propene and chemical grade propene as described, for example, by WO 2004/007405.

The oxygen source used is normally air (optionally together with cycle gas).

The partial oxidation using the catalysts of the invention obtainable as described (for example the annular shaped unsupported catalyst bodies) can be conducted in the simplest case, for example, in a single-zone multiple catalyst tube fixed bed reactor as described in DE-A 44 31 957, EP-A 700 714 and EP-A 700 893.

Customarily, in the aforementioned shell and tube reactors, the catalyst tubes are manufactured from ferritic steel and typically have a wall thickness of 1 to 3 mm. Their internal diameter is generally from 20 to 30 mm, frequently from 21 to 26 mm. A typical catalyst tube length is, for example, 3.20 m. Appropriately in application terms, the number of catalyst tubes accommodated in the shell and tube vessel runs to at least 1000, preferably to at least 5000. Frequently, the number of catalyst tubes accommodated in the reaction vessel is 15 000 to 40 000. Shell and tube reactors having a number of catalyst tubes exceeding 45 000 are usually exceptional. Within the vessel, the catalyst tubes are normally arranged in homogeneous distribution, the distribution appropriately being selected such that the separation of the central internal axes of mutually adjacent catalyst tubes (called the catalyst tube pitch) is 35 to 45 mm (cf. EP-B 468 290).

The partial oxidation can alternatively be conducted in a multizone (for example "two-zone") multiple catalyst tube fixed bed reactor as recommended by DE-A 199 10 506, DE-A 103 13 213, DE-A 103 13 208 and EP-A 1 106 598, particularly at elevated space velocities of the organic compound to be partially oxidized on the catalyst charge of the multiple catalyst tube reactor. A typical catalyst tube length in the case of a two-zone multiple catalyst tube fixed bed reactor is 3.50 m. Everything else is essentially as described for the one-zone multiple catalyst tube fixed bed reactor. In each temperature control zone (the one-zone multiple catalyst tube reactor fixed bed reactor has just one temperature control zone) of the one-zone or multizone multiple catalyst tube fixed bed reactor, a heat exchange medium is conducted around the catalyst tubes within which the catalyst charge (the fixed catalyst bed) is present. Suitable examples of heat exchange media are melts of salts such as potassium nitrate, potassium nitrite, sodium nitrite and/or sodium nitrate, or of low-melting metals such as sodium, mercury and alloys of different metals. The flow rate of the heat exchange medium within the respective temperature control zone is generally chosen such that the temperature of the heat exchange medium rises from the entry point into the temperature control zone to the exit point from the temperature control zone by 0 to 15° C., frequently 1 to 10° C., or 2 to 8° C., or 3 to 6° C.

The inlet temperature of the heat exchange medium which, viewed over the respective temperature control zone, can be guided in cocurrent or countercurrent to the reaction gas mixture is preferably chosen as recommended in documents EP-A 1 106 598, DE-A 199 48 523, DE-A 199 48 248, DE-A 103 13 209, EP-A 700 714, DE-A 103 13 208, DE-A 103 13 213, WO 00/53557, WO 00/53558, WO 01/36364, WO 00/53557 and the other documents cited as prior art in these documents. Within the temperature control zone, the heat exchange medium is preferably guided in a meandering manner. The difference between the highest and lowest temperatures of the heat exchange medium within a temperature control zone should, considered over that length section of the temperature control zone in which there is a catalytically active section (not a pure inert bed) of the fixed catalyst bed, advantageously be ≥0° C. and ≤5° C. (this difference is preferably small). In general, the multiple catalyst tube fixed bed reactor additionally has thermal tubes for determination of the temperature of the reaction gas in the catalyst bed (thermal tubes and reaction tubes are charged with the same fixed bed). In an appropriate manner, the internal diameter of the thermal tubes and the diameter of the receiving well (thermowell) for the thermocouple which is centered within it and runs parallel to the longitudinal axis of the thermal tube is chosen such that the ratio of volume that evolves heat of reaction to heat-removing surface area in thermal tubes and working tubes is the same or only slightly different.

The pressure drop in the case of working tubes and thermal tubes should be the same, based on the same GHSV (=strength of the volume flow rate of the reaction gas mixture entering the tube divided by the bed volume of the fixed catalyst bed present in the tube). Compensation of pressure drop in a thermal tube can be effected, for example, by adding catalyst spall to the shaped catalyst bodies. This compensation is appropriately effected homogeneously over the entire thermal tube length. For the rest, the filling of the thermal tubes can be configured as described in EP-A 873783.

For provision of the catalyst charge in the catalyst tubes, as already mentioned, it is possible to use solely catalysts of the invention, in annular form for example, obtainable as described (for example the annular shaped unsupported catalyst bodies), or else, for example, largely homogeneous mixtures of shaped catalyst bodies of the invention (for example the annular shaped unsupported catalyst bodies) obtainable as described and no shaped bodies that include active composition and are essentially inert with regard to the heterogeneously catalyzed partial gas phase oxidation. Useful materials for such inert shaped bodies include, for example, porous or nonporous aluminum oxides, silicon dioxide, zirconium dioxide, silicon carbide, silicates such as magnesium or aluminum silicate and/or steatite (for example of the C220 type from CeramTec, Germany).

The geometry of such shaped inert diluent bodies may in principle be as desired. This means that they may, for example, be spheres, polygons, solid cylinders or else, as in the case of annular shaped catalyst bodies for example, rings. Frequently, the inert shaped diluent bodies chosen will be those whose geometry corresponds to that of the shaped catalyst bodies to be diluted therewith. Along the catalyst charge, however, the geometry of the shaped catalyst body may also be changed or shaped catalyst bodies of different geometry may be used in a largely homogeneous blend. In a less preferred procedure, the active composition of the shaped catalyst body may also be altered along the catalyst charge.

Quite generally, the catalyst charge is advantageously configured such that the volume-specific activity (i.e. that normalized to the unit of volume) either remains constant or increases (continuously, abruptly or in stages) in flow direction of the reaction gas mixture.

A reduction in the volume-specific activity can be achieved in a simple manner, for example, by homogeneously diluting a basic amount of shaped catalyst bodies produced uniformly in accordance with the invention, in annular form for example (for example annular shaped unsupported catalyst bodies), with inert shaped diluent bodies. The higher the proportion of shaped diluent bodies chosen, the smaller the amount of active composition or catalyst activity present in a particular volume of the charge. A reduction can also be achieved by altering the geometry of the shaped catalyst bodies obtainable in accordance with the invention in such a way that the amount of active composition present in the unit of the inner reaction tube volume becomes smaller.

For the heterogeneously catalyzed gas phase partial oxidations with shaped catalyst bodies, for example in annular form, obtainable as described in accordance with the invention (for example annular shaped unsupported catalyst bodies), the catalyst charge is preferably either configured over its entire length homogeneously with just one type of shaped catalyst bodies (for example one type of annular shaped unsupported catalyst bodies) or configured as follows. At the reactor inlet, over a length of 10% to 60%, preferably 10% to 50%, more preferably 20% to 40% and most preferably 25% to 35% (i.e., for example, at a length of 0.70 to 1.50 m, preferably 0.90 to 1.20 m), in each case of the total length of the catalyst charge, an essentially homogeneous mixture of shaped catalyst bodies obtainable in accordance with the invention (for example annular shaped unsupported catalyst bodies) and inert shaped diluent bodies (both preferably having essentially the same geometry) is positioned, where the proportion by weight of the shaped diluent bodies (the bulk densities of shaped catalyst bodies and of shaped diluent bodies generally differ only slightly) is normally 5% to 40% by weight, or 10% of 40% by weight, or 20% to 40% by weight, or 25% to 35% by weight. This first charge section is then advantageously followed, up to the end of the length of the catalyst charge (i.e., for example, over a length of 1.00 to 3.00 m or of 1.00 to 2.70 m, preferably 1.40 to 3.00 m, or 2.00 to 3.00 m), either by a bed of the same shaped catalyst body of the invention obtainable as described (for example annular shaped unsupported catalyst bodies) diluted merely to a lesser degree (than in the first section), or, most preferably, a 100% (undiluted) bed of the same shaped catalyst body of the invention (for example annular shaped unsupported catalyst body) that has also been used in the first section. It is of course also possible to choose a constant dilution over the entire charge. It is also possible to charge the first section merely with a shaped catalyst body obtainable in accordance with the invention (for example annular shaped unsupported catalyst body) of low active composition density based on its occupation of space, and the second section with a shaped catalyst body obtainable in accordance with the invention (for example annular shaped unsupported catalyst body) with a high active composition density based on its occupation of space (for example 6.5 mm×3 mm×4.5 mm [external diameter× height×internal diameter] in the first section, and 5×2×2 mm [E×H×I] in the second section).

In flow direction of the reaction gas mixture upstream of the actual fixed bed catalyst charge, a bed of inert shaped bodies may be provided, which pursues the purpose, for example, of increasing the inlet temperature of the reaction gas mixture to the temperature of the heat exchange medium.

Moreover, according to the teachings of the prior art (for example WO 2012/049246), the catalyst charge (especially the fresh catalyst charge) of the reactor and the process conditions for the catalyst partial oxidation, in the case of a heterogeneously catalyzed partial oxidation of propene to acrolein (or in the case of a heterogeneously catalyzed partial oxidation for preparation of methacrolein), are preferably chosen (configured) such that, in partial oxidation operation, there is no point in the fixed catalyst bed at which the difference between the fixed catalyst bed temperature at this point and the temperature of the heat exchange medium at the level of this point is $\geq 120°$ C. Advantageously, however, this temperature difference at every point, in the positive direction, is $\leq 100°$ C. (especially 40 to 100° C.), particularly advantageously $\leq 90°$ C. (especially 50 to 90° C.). In principle, however, this (positive) temperature difference may also be $\leq 50°$ C. or $\leq 40°$ C. Moreover, the configuration is preferably such that this temperature difference, in the event of an increase in the temperature of the heat exchange medium by 1° C., rises at any point in the fixed catalyst bed by $>0°$ C. but $\leq +9°$ C., better $\leq +7°$ C., preferably $\leq +5°$ C., more preferably $\leq +3°$ C. (see also EP-A 1106598).

Otherwise, a heterogeneously catalyzed partial oxidation for preparation of acrolein (from propene) or from methacrolein (from the $C_4$ precursor compounds mentioned in the present document) with annular shaped unsupported catalyst bodies produced in accordance with the invention can advantageously be executed in an entirely corresponding manner to the details in WO 2015/067656.

Overall, in the case of a partial oxidation for preparation of acrolein or methacrolein conducted with the shaped catalyst bodies (for example in annular form) (for example annular shaped unsupported catalyst bodies) obtainable in accordance with the invention as described as catalysts, the catalyst charge, the starting reaction gas mixture, the space velocity and the reaction temperature are generally chosen so as to result in, in a single pass of the reaction gas mixture through the catalyst charge, a conversion of the organic compound to be partially oxidized (propene, isobutene, tert-butanol or the methyl ether thereof) of at least 90 mol %, or at least 92 mol %, preferably of at least 93 mol % or at least 94 mol %, or at least 95 mol % or at least 97 mol %, but normally $\leq 99$ mol %. The selectivity of acrolein or methacrolein formation here will regularly be 80 mol %, or 85 mol % or $\geq 90$ mol %. The aim will naturally be minimum hotspot temperatures.

Finally, it should be emphasized that annular shaped unsupported catalyst bodies of the invention that are obtainable as described also have advantageous fracture characteristics in reactor charging.

The startup of a fresh catalyst charge (fixed catalyst bed) comprising geometric shaped catalyst bodies obtainable in accordance with the invention (for example annular shaped unsupported catalyst bodies) can be effected, for example, as described in DE-A 103 37 788 or in DE-A 102009047291.

The forming of geometric shaped catalyst bodies obtainable in accordance with the invention can be accelerated by conducting it at essentially homogeneous conversion at elevated space velocity of reaction gas input mixture on the catalyst charge.

Otherwise, multimetal oxide compositions of the general stoichiometry I obtainable in accordance with the invention and catalysts comprising them as active composition are quite generally suitable for catalysis of the gas phase partial (amm)oxidation of an alkanol, alkanal, alkene, alkane and alkenal having 3 to 6 (i.e. 3, 4, 5 or 6) carbon atoms to olefinically unsaturated aldehydes and/or carboxylic acids, for example, and the corresponding nitriles, and for oxidative dehydrogenations on the gas phase catalysis of the aforementioned organic compounds comprising 3, 4, 5 or 6 carbon atoms.

Appropriately for application purposes, the industrial scale production of annular shaped unsupported catalyst bodies of the invention is effected analogously to the manner described in German published specifications DE-A 102008040093 and DE-A 102008040094 (particularly advantageously as in the illustrative embodiments of these documents).

Thus, the present application comprises especially the following embodiments of the invention:

1. A multimetal oxide composition comprising Mo, Bi, Fe and Cu and having the general stoichiometry I

$$Mo_{12}Bi_aFe_bCu_cCo_dNi_eW_fG_gH_hL_lM_mO_x \qquad (I),$$

in which the variables are each defined as follows:
G=one element or more than one element from the group consisting of K, Na, Rb and Cs,
H=one element or more than one element from the group consisting of Ba, Ca, Cr, Ce, La, Mg, Mn, Pb, Sn, Sr and Zn,
L=one element or more than one element from the group consisting of B, Nb, P, Sb, Ta, Te, Ti, Y and Zr,
M=one element or more than one element from the group consisting of Al and Si,
a=0.2 to 2.5,
b=0.5 to 4,
c=0.05 to 0.55,
d+e=4 to 11,
f=0 to 1.2,
g=0.03 to 0.5,
h=0 to 20,
l=0 to 10,
m=0 to 800, and
x=a number which is determined by the valency and frequency of the elements in I other than oxygen,
which fulfill the following conditions:

$$12/(d+e+1.5 \cdot b+h)=0.8 \text{ to } 2, \text{ and}$$

$$a \cdot c = 0.01 \text{ to } 1.5.$$

2. The multimetal oxide composition according to embodiment 1, wherein the stoichiometric coefficient c is 0.05 to 0.5.
3. The multimetal oxide composition according to embodiment 1 or 2, wherein the stoichiometric coefficient c is 0.05 to 0.45.
4. The multimetal oxide composition according to any of embodiments 1 to 3, wherein the stoichiometric coefficient c is 0.05 to 0.4.
5. The multimetal oxide composition according to any of embodiments 1 to 4, wherein the stoichiometric coefficient c is 0.05 to 0.35.
6. The multimetal oxide composition according to any of embodiments 1 to 5, wherein the stoichiometric coefficient c is 0.1 to 0.3.
7. The multimetal oxide composition according to any of embodiments 1 to 6, wherein the stoichiometric coefficient c is 0.15 to 0.25.
8. The multimetal oxide composition according to any of embodiments 1 to 7, wherein the stoichiometric coefficient c is 0.2.
9. The multimetal oxide composition according to any of embodiments 1 to 8, wherein the product P=a·c fulfills the condition P=0.03 to 1.3.
10. The multimetal oxide composition according to any of embodiments 1 to 9, wherein the product P=a·c fulfills the condition P=0.05 to 1.
11. The multimetal oxide composition according to any of embodiments 1 to 10, wherein the product P=a·c fulfills the condition P=0.075 to 0.75.
12. The multimetal oxide composition according to any of embodiments 1 to 11, wherein the product P=a·c fulfills the condition P=0.09 to 0.5.
13. The multimetal oxide composition according to any of embodiments 1 to 12, wherein the product P=a·c fulfills the condition P=0.1 to 0.3.
14. The multimetal oxide composition according to any of embodiments 1 to 13, wherein the quotient $Q^2=d/(d+e)$ fulfills the condition $Q^2=0.45$ to 1.
15. The multimetal oxide composition according to any of embodiments 1 to 14, wherein the quotient $Q^2=d/(d+e)$ fulfills the condition $Q^2=0.6$ to 1.
16. The multimetal oxide composition according to any of embodiments 1 to 15, wherein the quotient $Q^2=d/(d+e)$ fulfills the condition $Q^2=0.7$ to 1.
17. The multimetal oxide composition according to any of embodiments 1 to 16, wherein the quotient $Q^2=d/(d+e)$ fulfills the condition $Q^2=0.8$ to 1.
18. The multimetal oxide composition according to any of embodiments 1 to 17, wherein the quotient $Q^2=d/(d+e)$ fulfills the condition $Q^2=0.9$ to 1.
19. The multimetal oxide composition according to any of embodiments 1 to 18, wherein the quotient $Q^2=d/(d+e)$ fulfills the condition $Q^2=1$.
20. The multimetal oxide composition according to any of embodiments 1 to 19, wherein the quotient $Q^1=12/(d+e+1.5 \cdot b+h)$ fulfills the condition $Q^1=0.9$ to 1.75.
21. The multimetal oxide composition according to any of embodiments 1 to 20, wherein the quotient $Q^1=12/(d+e+1.5 \cdot b+h)$ fulfills the condition $Q^1=0.95$ to 1.5.
22. The multimetal oxide composition according to any of embodiments 1 to 21, wherein the quotient $Q^1=12/(d+e+1.5 \cdot b+h)$ fulfills the condition $Q^1=1$ to 1.3.
23. The multimetal oxide composition according to any of embodiments 1 to 22, wherein the quotient $Q^1=12/(d+e+1.5 \cdot b+h)$ fulfills the condition $Q^1=1$ to 1.2.
24. The multimetal oxide composition according to any of embodiments 1 to 23, wherein the quotient $Q^1=12/(d+e+1.5 \cdot b+h)$ fulfills the condition $Q^1=1$ to 1.1.
25. The multimetal oxide composition according to any of embodiments 1 to 24, wherein the quotient $Q^3=b/(b+d+e+h)$ fulfills the condition $Q^3=0.05$ to 0.4.
26. The multimetal oxide composition according to any of embodiments 1 to 25, wherein the quotient $Q^3=b/(b+d+e+h)$ fulfills the condition $Q^3=0.1$ to 0.4.
27. The multimetal oxide composition according to any of embodiments 1 to 26, wherein the quotient $Q^3=b/(b+d+e+h)$ fulfills the condition $Q^3=0.2$ to 0.4.
28. The multimetal oxide composition according to any of embodiments 1 to 27, wherein the quotient $Q^3=b/(b+d+e+h)$ fulfills the condition $Q^3=0.25$ to 0.35.
29. The multimetal oxide composition according to any of embodiments 1 to 28, wherein the quotient $Q^3=b/(b+d+e+h)$ fulfills the condition $Q^3=0.3$.
30. The multimetal oxide composition according to any of embodiments 1 to 29, wherein the stoichiometric coefficient a is 0.5 to 3.
31. The multimetal oxide composition according to any of embodiments 1 to 30, wherein the stoichiometric coefficient a is 0.5 to 2.
32. The multimetal oxide composition according to any of embodiments 1 to 31, wherein the stoichiometric coefficient a is 0.5 to 1.5.
33. The multimetal oxide composition according to any of embodiments 1 to 32, wherein the stoichiometric coefficient a is 0.5 to 1.

34. The multimetal oxide composition according to any of embodiments 1 to 33, wherein the stoichiometric coefficient a is 0.5 to 0.75.
35. The multimetal oxide composition according to any of embodiments 1 to 34, wherein the stoichiometric coefficient a is 0.6.
36. The multimetal oxide composition according to any of embodiments 1 to 35, wherein the stoichiometric coefficient b is 0.5 to 3.5.
37. The multimetal oxide composition according to any of embodiments 1 to 36, wherein the stoichiometric coefficient b is 1 to 3.5.
38. The multimetal oxide composition according to any of embodiments 1 to 37, wherein the stoichiometric coefficient b is 1.5 to 3.5.
39. The multimetal oxide composition according to any of embodiments 1 to 38, wherein the stoichiometric coefficient b is 2 to 3.
40. The multimetal oxide composition according to any of embodiments 1 to 39, in which the sum of d+e is 5 to 11.
41. The multimetal oxide composition according to any of embodiments 1 to 40, in which the sum of d+e is 6 to 10.
42. The multimetal oxide composition according to any of embodiments 1 to 41, in which the sum of d+e is 6.5 to 9.5.
43. The multimetal oxide composition according to any of embodiments 1 to 42, in which the sum of d+e is 7 to 9.
44. The multimetal oxide composition according to any of embodiments 1 to 43, wherein the stoichiometric coefficient g is 0.04 to 0.4.
45. The multimetal oxide composition according to any of embodiments 1 to 44, wherein the stoichiometric coefficient g is 0.04 to 0.3.
46. The multimetal oxide composition according to any of embodiments 1 to 45, wherein the stoichiometric coefficient g is 0.04 to 0.25.
47. The multimetal oxide composition according to any of embodiments 1 to 46, wherein the stoichiometric coefficient g is 0.05 to 0.15.
48. The multimetal oxide composition according to any of embodiments 1 to 47, wherein the stoichiometric coefficient g is 0.06 to 0.13.
49. The multimetal oxide composition according to any of embodiments 1 to 48, wherein the stoichiometric coefficient g is 0.08.
50. The multimetal oxide composition according to any of embodiments 1 to 49, wherein the stoichiometric coefficient h is 0 to 15.
51. The multimetal oxide composition according to any of embodiments 1 to 50, wherein the stoichiometric coefficient h is 0 to 10.
52. The multimetal oxide composition according to any of embodiments 1 to 51, wherein the stoichiometric coefficient h is 0 to 5.
53. The multimetal oxide composition according to any of embodiments 1 to 52, wherein the stoichiometric coefficient h is 0 to 2.5.
54. The multimetal oxide composition according to any of embodiments 1 to 53, wherein the stoichiometric coefficient l is 0 to 8.
55. The multimetal oxide composition according to any of embodiments 1 to 54, wherein the stoichiometric coefficient l is 0 to 6.
56. The multimetal oxide composition according to any of embodiments 1 to 55, wherein the stoichiometric coefficient l is 0 to 4.
57. The multimetal oxide composition according to any of embodiments 1 to 56, wherein the stoichiometric coefficient l is 0 to 2.
58. The multimetal oxide composition according to any of embodiments 1 to 57, wherein the stoichiometric coefficient m is 0.1 to 500.
59. The multimetal oxide composition according to any of embodiments 1 to 58, wherein the stoichiometric coefficient m is 0.2 to 100.
60. The multimetal oxide composition according to any of embodiments 1 to 59, wherein the stoichiometric coefficient m is 0.3 to 50.
61. The multimetal oxide composition according to any of embodiments 1 to 60, wherein the stoichiometric coefficient m is 0.4 to 30.
62. The multimetal oxide composition according to any of embodiments 1 to 61, wherein the stoichiometric coefficient m is 0.5 to 20.
63. The multimetal oxide composition according to any of embodiments 1 to 62, wherein the stoichiometric coefficient m is 0.6 to 10.
64. The multimetal oxide composition according to any of embodiments 1 to 63, wherein the stoichiometric coefficient m is 0.7 to 7.
65. The multimetal oxide composition according to any of embodiments 1 to 64, wherein the stoichiometric coefficient m is 0.8 to 5.
66. The multimetal oxide composition according to any of embodiments 1 to 65, wherein the stoichiometric coefficient m is 1 to 3.6.
67. The multimetal oxide composition according to any of embodiments 1 to 66, in which the variable G has the definition G =one element or more than one element from the group consisting of Cs, K and Na.
68. The multimetal oxide composition according to any of embodiments 1 to 67, in which the variable G has the definition G=one element or more than one element from the group consisting of K and Na.
69. The multimetal oxide composition according to any of embodiments 1 to 68, in which the variable G has the definition G=K.
70. The multimetal oxide composition according to any of embodiments 1 to 69, in which the variable M has the definition M=Si.
71. The multimetal oxide composition according to any of embodiments 1 to 70, in which the variable H has the definition H=one element or more than one element from the group consisting of Ca, Ce, Mg, Mn, Sn, Sr and Zn.
72. The multimetal oxide composition according to any of embodiments 1 to 71, in which the variable H has the definition H=one element or more than one element from the group consisting of Ce, Mg, Mn and Zn.
73. The multimetal oxide composition according to any of embodiments 1 to 72, in which the variable H has the definition H=one element or more than one element from the group consisting of Ce, Mg, Mn and Zn.
74. The multimetal oxide composition according to any of embodiments 1 to 73, in which the variable L has the definition L=one element or more than one element from the group consisting of Nb, P, Sb, Te and Zr.
75. The multimetal oxide composition according to any of embodiments 1 to 74, in which the variable L has the definition L=one element or more than one element from the group consisting of P, Ti and Zr.

76. The multimetal oxide composition according to any of embodiments 1 to 75, wherein the specific surface area is 2 to 20 m$^2$/g.

77. The multimetal oxide composition according to any of embodiments 1 to 76, wherein the specific surface area is 2 to 15 m$^2$/g.

78. The multimetal oxide composition according to any of embodiments 1 to 77, wherein the specific surface area is 3 to 10 m$^2$/g.

79. The multimetal oxide composition according to any of embodiments 1 to 76, wherein the specific surface area is 4 to 8 m$^2$/g.

80. The multimetal oxide composition according to any of embodiments 1 to 79, wherein the total pore volume is in the range from 0.1 to 1 cm$^3$/g.

81. The multimetal oxide composition according to any of embodiments 1 to 80, wherein the total pore volume is in the range from 0.1 to 0.8 cm3/g.

82. The multimetal oxide composition according to any of embodiments 1 to 81, wherein the total pore volume is in the range from 0.1 to 0.6 cm$^3$/g.

83. The multimetal oxide composition according to any of embodiments 1 to 82, wherein the total pore volume is in the range from 0.2 to 0.5 cm$^3$/g.

84. The multimetal oxide composition according to any of embodiments 1 to 83, in which the contribution of pores having a pore radius ≤0.1 μm to the total pore volume is ≤0.05 cm$^3$/g.

85. The multimetal oxide composition according to any of embodiments 1 to 84, in which the contribution of pores having a pore radius in the range from 0.2 to 0.4 μm to the total pore volume, based on the total pore volume, is 70% by volume.

86. The multimetal oxide composition according to any of embodiments 1 to 85, in which the contribution of pores having a pore radius in the range from 0.2 to 0.4 μm to the total pore volume, based on the total pore volume, is ≥75% by volume.

87. The multimetal oxide composition according to any of embodiments 1 to 86, in which the contribution of pores having a pore radius in the range from 0.2 to 0.4 μm to the total pore volume, based on the total pore volume, is ≥85% by volume.

88. The multimetal oxide composition according to any of embodiments 1 to 87, in which the contribution of pores having a pore radius in the range from 0.2 to 0.4 μm to the total pore volume, based on the total pore volume, is ≥90% by volume.

89. The multimetal oxide composition according to any of embodiments 1 to 88, in which the contribution of pores having a pore radius in the range from 0.2 to 0.4 μm to the total pore volume, based on the total pore volume, is ≥95% by volume.

90. The multimetal oxide composition according to any of embodiments 1 to 87, in which the contribution of pores having a pore radius in the range from 0.2 to 0.4 μm to the total pore volume, based on the total pore volume, is ≥98% by volume.

91. The multimetal oxide composition according to any of embodiments 1 to 90, in which a plot of its pore diameters in μm on the abscissa and the logarithm of the differential contribution in cm$^3$/g of the respective pore diameter to the total pore volume in cm$^3$/g on the ordinate results in an essentially monomodal distribution curve.

92. An eggshell catalyst comprising a shaped support body and a shell of at least one multimetal oxide composition according to any of embodiments 1 to 91 present on the outer surface of the shaped support body.

93. The eggshell catalyst according to embodiment 92, in which the eggshell composed of the at least one multimetal oxide composition has a thickness of 10 to 1000 μm.

94. The eggshell catalyst according to embodiment 92 or 93, in which the eggshell composed of the at least one multimetal oxide composition has a thickness of 100 to 700 μm.

95. The eggshell catalyst according to any of embodiments 92 to 94, in which the eggshell composed of the at least one multimetal oxide composition has a thickness of 300 to 500 μm.

96. The eggshell catalyst according to any of embodiments 92 to 95, wherein the shaped support body is a sphere, a solid cylinder or a hollow cylinder.

97. The eggshell catalyst according to any of embodiments 92 to 96, wherein the shaped support body is a sphere having a diameter of 1 to 8 mm.

98. The eggshell catalyst according to any of embodiments 92 to 97, wherein the shaped support body is a sphere having a diameter of 4 to 5 mm.

99. The eggshell catalyst according to any of embodiments 92 to 96, wherein the shaped support body is a cylinder having a length of 2 to 10 mm and an external diameter of 4 to 10 mm.

100. The eggshell catalyst according to any of embodiments 92 to 96, wherein the shaped support body is a ring having a wall thickness of 1 to 4 mm, a length of 2 to 10 mm and an external diameter of 4 to 10 mm.

101. The eggshell catalyst according to embodiment 100, wherein the shaped support body is a ring having a wall thickness of 1 to 2 mm, a length of 3 to 6 mm and an external diameter of 4 to 8 mm.

102. The eggshell catalyst according to embodiment 100, wherein the shaped support body is a ring having a wall thickness of 1 to 2 mm, a length of 2 to 4 mm and an external diameter of 4 to 8 mm.

103. The eggshell catalyst according to any of embodiments 92 to 102, wherein the material for the shaped support body is aluminum oxide, silicon oxide, a silicate, silicon carbide, zirconium dioxide, thorium dioxide or steatite.

104. A shaped unsupported catalyst body, the active composition of which is a multimetal oxide composition according to any of embodiments 1 to 91.

105. The shaped unsupported catalyst body according to embodiment 104 having the geometry of a sphere, a cylinder or a ring.

106. The unsupported catalyst according to embodiment 105 having the geometry of a sphere having a diameter of 2 to 10 mm.

107. The unsupported catalyst according to embodiment 105 having the geometry of a sphere having a diameter of 2 to 8 mm.

108. The unsupported catalyst according to embodiment 105 having the geometry of a sphere having a diameter of 4 to 8 mm.

109. The unsupported catalyst according to embodiment 105 having the geometry of a cylinder having a length of 2 to 10 mm and an external diameter of 2 to 10 mm.

110. The unsupported catalyst according to embodiment 105 having the geometry of a cylinder having a length of 2 to 8 mm and an external diameter of 2 to 8 mm.

111. The unsupported catalyst according to embodiment 105 having the geometry of a cylinder having a length of 3 to 8 mm and an external diameter of 3 to 8 mm.
112. The unsupported catalyst according to embodiment 105 having the geometry of a ring having a wall thickness of 1 to 3 mm, a length of 2 to 10 mm and an external diameter of 2 to 10 mm.
113. The unsupported catalyst according to embodiment 105 having the geometry of a ring having a wall thickness of 1 to 3 mm, a length of 2 to 8 mm and an external diameter of 2 to 8 mm.
114. The unsupported catalyst according to embodiment 105 having the geometry of a ring having a wall thickness of 1 to 3 mm, a length of 3 to 8 mm and an external diameter of 3 to 8 mm.
115. The shaped unsupported catalyst body according to any of embodiments 112 to 114, in which the ratio of length to external diameter is 0.3 to 1.5.
116. The shaped unsupported catalyst body according to any of embodiments 112 to 115, in which the ratio of length to external diameter is 0.3 to 1.2.
117. The shaped unsupported catalyst body according to any of embodiments 112 to 115, in which the ratio of length to external diameter is 0.5 to 1.1.
118. The shaped unsupported catalyst body according to any of embodiments 112 to 117, in which the ratio of length to external diameter is 0.5 to 1.0.
119. The shaped unsupported catalyst body according to any of embodiments 112 to 118, in which the ratio of internal diameter to external diameter is 0.3 to 1.5.
120. The shaped unsupported catalyst body according to any of embodiments 112 to 119, in which the ratio of internal diameter to external diameter is 0.6 to 1.1.
121. The shaped unsupported catalyst body according to embodiment 112, wherein the ring geometry with external diameter×length×internal diameter is a ring geometry from the group of 5 mm×5 mm×2 mm, 5 mm×2 mm×2 mm, 5 mm×3 mm×2 mm, 5 mm×5 mm×2.5 mm, 5 mm×3 mm×2.5 mm, 5.5 mm×5.5 mm×2.5 mm, 5.5 mm×5.5 mm×3 mm, 5 mm×3 mm×3 mm, 5.5 mm×3 mm×3.5 mm, 6 mm×3 mm×4 mm, 6 mm×6 mm×3 mm, 6 mm×6 mm×3.5 mm, 6.5 mm×3 mm×4.5 mm, 7 mm×3 mm×5 mm, 7 mm×7 mm×3 mm, 7 mm×3 mm×4 mm and 7 mm×7 mm×4 mm.
122. A process for producing a multimetal oxide composition according to any of embodiments 1 to 91, which comprises producing a finely divided intimate dry mixture from sources of the elemental constituents thereof and calcining it at temperatures in the range from 350° C. to 650° C.
123. A process for producing a multimetal oxide composition according to any of embodiments 1 to 91, which comprises producing a finely divided intimate dry mixture from sources of the elemental constituents thereof and calcining it at temperatures in the range from 350° C. to 600° C.
124. A process for producing a multimetal oxide composition according to any of embodiments 1 to 91, which comprises producing a finely divided intimate dry mixture from sources of the elemental constituents thereof and calcining it at temperatures in the range from 350° C. to 550° C.
125. A process for producing a multimetal oxide composition according to any of embodiments 1 to 91, which comprises producing a finely divided intimate dry mixture from sources of the elemental constituents thereof and calcining it at temperatures in the range from 350° C. to 530° C.
126. The process according to embodiment 125, wherein the calcination is effected under inert gas, under an oxidizing atmosphere, under a reducing atmosphere or under reduced pressure.
127. The process according to embodiment 126, wherein the calcination is effected under air.
128. The process according to any of embodiments 122 to 127, wherein the sources in the form of solutions and/or suspensions are mixed with one another and the resulting wet mixture M is dried to give the finely divided intimate dry mixture.
129. The process according to embodiment 128, wherein the solvent and/or suspension medium is water or an aqueous solution and the resulting wet mixture M is an aqueous mixture M.
130. The process according to embodiment 128 or 129, wherein the sources used are solely solutions and/or colloidal solutions.
131. The process according to embodiment 130, wherein one source is an aqueous solution A comprising at least one dissolved starting compound of the elements Fe, Bi and Cu and at least one dissolved starting compound of at least one of the elements Co and Ni, and having a pH of ≤3 and ≥−2.
132. The process according to embodiment 131, wherein the starting compounds of the elements Fe, Bi and Cu and at least one of the elements Co and Ni that are present in dissolved form in the aqueous solution A are the nitrates and/or nitrate hydrates thereof.
133. The process according to embodiment 131 or 132, wherein the total content in aqueous solution A of metal constituents (metal elements), based on the amount of aqueous solution A, is 5% to 20% by weight.
134. The process according to any of embodiments 130 to 133, wherein one source is an aqueous solution B comprising at least one dissolved starting compound of the element Mo and one or more dissolved sources of at least one of the elements K, Na, Rb and Cs, and having a pH of <7 and ≥3.
135. The process according to embodiment 134, wherein at least one starting compound of the element Mo is ammonium heptamolybdate tetrahydrate.
136. The process according to embodiment 134 or 135, wherein at least one starting compound of at least one of the elements K, Na, Rb and Cs is the element hydroxide.
137. The process according to any of embodiments 134 to 136, wherein the total content in aqueous solution B of Mo, based on the amount of aqueous solution B, is 2% to 25% by weight.
138. The process according to any of embodiments 130 to 137, wherein one source is aqueous silica sol.
139. The process according to any of embodiments 130 to 138, wherein, in the course of production of the finely divided intimate dry mixture, an aqueous solution A comprising at least one dissolved starting compound of the elements Fe, Bi and Cu and at least one dissolved starting compound of at least one of the elements Co and Ni, and having a pH of ≤3 and ≥−2, is mixed with an aqueous solution B comprising at least one dissolved starting compound of the element Mo and one or more dissolved sources of at least one of the elements K, Na, Rb and Cs, and having a pH of <7 and ≥3, to give an aqueous mixture.

140. The process according to embodiment 139, wherein the mixing is effected by stirring aqueous solution A into aqueous solution B.
141. The process according to embodiment 140 or 141, wherein the mixing is effected at a temperature of $\leq 80°$ C. and $\geq 0°$ C.
142. The process according to any of embodiments 139 to 141, wherein the mixing is effected at a temperature of $\leq 75°$ C. and $\geq 30°$ C.
143. The process according to any of embodiments 139 to 142, wherein the mixing is effected at a temperature of $\leq 70°$ C. and $\geq 50°$ C.
144. The process according to any of embodiments 139 to 143, wherein the mixing is effected at a temperature of $\leq 65°$ C. and $\geq 55°$ C.
145. The process according to any of embodiments 139 to 144, wherein the ratio V formed from the total molar amount $n_1$ of $NH_3$ and $NH^{4+}$ optionally present in the aqueous mixture of the aqueous solution A and the aqueous solution B and the total molar amount $n_2$ of Mo present in the same aqueous mixture, $V=n_1:n_2$, is $\leq 1.5$.
146. The process according to embodiment 145, wherein $V \leq 1$.
147. The process according to embodiment 145, wherein $V \leq 6/7$.
148. The process according to any of embodiments 139 to 147, wherein the pH of the aqueous mixture of aqueous solution A and aqueous solution B is $\leq 3$.
149. The process according to embodiment 148, wherein the pH of the aqueous mixture of aqueous solution A and aqueous solution B is $\geq 0$ and $\leq 2$.
150. The process according to any of embodiments 139 to 149, wherein an aqueous silica sol is mixed into the aqueous mixture of aqueous solution A and aqueous solution B, resulting in an aqueous mixture M as wet mixture M.
151. The process according to embodiment 150, wherein the $SiO_2$ content of the added aqueous silica sol is 15% to 60% by weight.
152. The process according to embodiment 150 or 151, wherein the $SiO_2$ content of the added aqueous silica sol is 20% to 60% by weight.
153. The process according to any of embodiments 150 to 152, wherein the $SiO_2$ content of the added aqueous silica sol is 30% to 60% by weight.
154. The process according to any of embodiments 150 to 153, wherein the $SiO_2$ content of the added aqueous silica sol is 40% to 60% by weight.
155. The process according to any of embodiments 150 to 154, wherein the $SiO_2$ content of the added aqueous silica sol is 45% to 55% by weight.
156. The process according to any of embodiments 150 to 155, wherein the total content in the aqueous mixture M of metal constituents (metal elements), based on the amount of the aqueous mixture M, is 3% to 20% by weight.
157. The process according to any of embodiments 150 to 156, wherein the total content in the aqueous mixture M of metal constituents (metal elements), based on the amount of the aqueous mixture M, is 5% to 15% by weight.
158. The process according to any of embodiments 150 to 157, wherein the proportion AT of the total molar amount of Co and/or Ni present in the aqueous mixture M which is in dissolved form in the aqueous mixture M is $\leq 50$ mol %.
159. The process according to embodiment 158, wherein AT$\leq 40$ mol %.
160. The process according to embodiment 158, wherein AT$\leq 30$ mol %.
161. The process according to embodiment 155, wherein AT$\leq 20$ mol %.
162. The process according to any of embodiments 158 to 161, wherein AT$\geq 10$ mol %.
163. The process according to any of embodiments 158 to 161, wherein AT$\leq 15$ mol %.
164. The process according to any of embodiments 150 to 163, wherein the pH of the aqueous mixture M is $\geq 0$ and $\geq 2$.
165. The process according to any of embodiments 128 to 164, wherein the drying is effected by spray drying.
166. The process according to any of embodiments 129 to 164, wherein the drying of the aqueous mixture M is effected by spray drying.
167. The process according to embodiment 166, wherein the spray drying of the aqueous mixture M is effected in a spray drier in which said aqueous mixture M is first divided into fine droplets and these are dried in a hot gas stream having an inlet temperature into the spray drier of 250 to 450° C.
168. The process according to embodiment 166 or 167, wherein the spray drying of the aqueous mixture M is effected in a spray drier in which said aqueous mixture M is first divided into fine droplets and these are dried in a hot gas stream having an inlet temperature into the spray drier of 270 to 370° C.
169. The process according to any of embodiments 166 to 168, wherein the outlet temperature of the gas stream from the spray drier is 100 to 160° C.
170. The process according to any of embodiments 166 to 169, wherein the spray drying is effected in cocurrent flow of the droplets relative to the hot gas.
171. The process according to any of embodiments 166 to 169, wherein the spray drying is effected in countercurrent flow of the droplets relative to the hot gas.
172. The process according to any of embodiments 166 to 169, wherein the intimate dry mixture, optionally with addition of shaping auxiliaries and optionally after coarsening, is shaped prior to the calcination to give shaped bodies of regular or irregular geometry.
173. The process according to embodiment 172, wherein the shaping is effected by tableting.
174. The process according to embodiment 172 or 173, wherein graphite is added as shaping auxiliary.
175. The process according to any of embodiments 172 to 174, wherein the shaped body has the geometry of a ring.
176. The process according to embodiment 175, wherein the ring has an external diameter of 2 to 10 mm, a height of 2 to 10 mm and a wall thickness of 1 to 3 mm.
177. The process according to embodiment 176, wherein the ring has an external diameter of 2 to 8 mm and a height of 2 to 8 mm.
178. The process according to embodiment 175 or 176, wherein the ring has an external diameter of 3 to 8 mm and a height of 3 to 8 mm.
179. The process according to any of embodiments 175 to 178, wherein the side crushing strength SD of the ring (of the annular shaped body) satisfies the relation 12 N$\leq$SD$\leq$40 N.

180. The process according to any of embodiments 175 to 179, wherein the side crushing strength SD of the ring (of the annular shaped body) satisfies the relation 15 N≤SD≤35 N.
181. The process according to any of embodiments 175 to 180, wherein the side crushing strength SD of the ring (of the annular shaped body) satisfies the relation 19 N≤SD≤32 N.
182. The process according to any of embodiments 122 to 181, wherein, prior to the calcination of the intimate dry mixture or of the shaped body shaped therefrom, optionally with addition of shaping auxiliaries and optionally after coarsening, the intimate dry mixture or the shaped body undergoes thermal treatment at temperatures of ≥120° C. and <350° C.
183. The process according to any of embodiments 122 to 182, wherein, prior to the calcination of the intimate dry mixture or of the shaped body shaped therefrom, optionally with addition of shaping auxiliaries and optionally after coarsening, the intimate dry mixture or the shaped body undergoes thermal treatment at temperatures of ≥150° C. and ≤320° C.
184. The process according to any of embodiments 122 to 183, wherein, prior to the calcination of the intimate dry mixture or of the shaped body shaped therefrom, optionally with addition of shaping auxiliaries and optionally after coarsening, the intimate dry mixture or the shaped body undergoes thermal treatment at temperatures of ≥170° C. and ≤290° C.
185. The multimetal oxide composition according to any of embodiments 1 to 91, which is not a composite composed of multiple layers of different multimetal oxide compositions.
186. An eggshell catalyst according to any of embodiments 92 to 103, wherein the eggshell of at least one multimetal oxide composition according to any of embodiments 1 to 91 present on the outer surface of the shaped support body is not a composite composed of multiple layers of different multimetal oxide compositions.
187. The shaped unsupported catalyst body according to any of embodiments 104 to 121, wherein the active composition is not a composite composed of multiple layers of different multimetal oxide compositions.
188. A process for heterogeneously catalyzed partial gas phase oxidation of an alkane, alkanol, alkanal, alkene and/or alkenal having 3 to 6 carbon atoms over a catalyst bed, wherein the catalyst bed includes at least one multimetal oxide composition according to any of embodiments 1 to 91 or according to embodiment 185.
189. A process for heterogeneously catalyzed partial gas phase oxidation of an alkane, alkanol, alkanal, alkene and/or alkenal having 3 to 6 carbon atoms over a catalyst bed, wherein the catalyst bed includes at least one catalyst according to any of embodiments 92 to 121 or according to embodiment 186 or 187.
190. A process for heterogeneously catalyzed partial gas phase oxidation of an alkane, alkanol, alkanal, alkene and/or alkenal having 3 to 6 carbon atoms over a catalyst bed, wherein the catalyst bed includes at least one product of a process according to any of embodiments 122 to 184.
191. The process according to embodiment 190, wherein the at least one product of a process according to any of embodiments 122 to 184 is not part of a composite composed of multiple layers of different multimetal oxide compositions.
192. The process according to any of embodiments 188 to 191, which is a process for heterogeneously catalyzed partial gas phase oxidation of propene to acrolein or of isobutene to methacrolein.
193. The process according to any of embodiments 188 to 191, which is a process for heterogeneously catalyzed partial ammoxidation of propene to acrylonitrile or of isobutene to methacrylonitrile.
194. The process according to any of embodiments 188 to 193, wherein the catalyst bed is a fixed catalyst bed.
195. The use of at least one multimetal oxide composition according to any of embodiments 1 to 91 or according to embodiment 185, or of at least one catalyst according to any of embodiments 92 to 121 or according to embodiment 186 or 187, or of at least one product of a process according to any of embodiments 122 to 184, for catalysis of a process for heterogeneously catalyzed partial gas phase oxidation of an alkane, alkanol, alkanal, alkene and/or alkenal having 3 to 6 carbon atoms over a catalyst bed.
196. The use according to embodiment 195, wherein the at least one product of a process according to any of embodiments 122 to 184 is not part of a composite composed of multiple layers of different multimetal oxide compositions.
197. The use according to embodiment 195 or 196, wherein the process for heterogeneously catalyzed partial oxidation is a process for heterogeneously catalyzed partial gas phase oxidation of propene to acrolein or of isobutene to methacrolein.
198. The use according to embodiment 195 or 196, wherein the process for heterogeneously catalyzed partial oxidation is a process for heterogeneously catalyzed partial ammoxidation of propene to acrylonitrile or of isobutene to methacrylonitrile.

INVENTIVE AND COMPARATIVE EXAMPLES

I. Preparation of inventive shaped unsupported catalyst bodies E1 to E8 and noninventive comparative shaped unsupported catalyst bodies C1 to C31
1. Preparation of the shaped unsupported catalyst body E1 wherein the active multimetal oxide has the stoichiometry $Mo_{12}Bi_{0.6}Fe_3Cu_{0.1}Co_7K_{0.08}Si_{1.6}$ (stoichiometry by starting weight present in the aqueous mixture M)

The stirred vessels used were each filled in the presence of ambient air. In the course of stirring/mixing, they were sealed airtight with a lid that had a pressure release valve to the atmosphere (1 atm, 1.01 bar).

a) Preparation of an Aqueous Solution B

A temperature-controllable stainless steel (EN 1.4541) cylindrical stirred vessel (capacity 10 L) equipped with an anchor stirrer was initially charged with 3.12 kg of demineralized water and heated to 60° C. while stirring (150 rpm).

Subsequently, with constant stirring and while maintaining the temperature of 60° C., 3.6 g of a 46.8% by weight aqueous potassium hydroxide solution (46.8% by weight of KOH) that had a temperature of 20° C. were added. While maintaining the 60° C., with constant stirring, 1137 g of fine granular ammonium heptamolybdate tetrahydrate (supplier: NIPPON INORGANIC COLOUR & CHEMICAL CO., LTD., 3-14-1 Funado Itabashi-ku Tokyo 174-0041 (JP); it had a turbidity, determined to WO 2016/147324 of 219 NTU) at a temperature of 25° C. were then stirred in in portions and the resulting aqueous solution (which was slightly turbid as a result of a tiny amount of insoluble isopolymolybdate contaminants) was stirred (150 rpm) at 60° C. for a further 20 min.

b) Preparation of an Aqueous Solution A

A temperature-controllable cylindrical stainless steel (EN 1.4541) stirred vessel (capacity 5 L) equipped with an anchor stirrer was initially charged with 1808 g of an aqueous cobalt(II) nitrate solution in nitric acid (12.4% by weight of Co, 27% by weight of nitrate ($NO3^-$), prepared by dissolving cobalt metal from MFT Metals % Ferro-Alloys Trading GmbH, D-41474 Viersen, purity >99.6% by weight of Co, <0.3% by weight of Ni, <100 mg/kg Fe, <50 mg/kg Cu in aqueous nitric acid), which were heated to 60° C. while stirring (150 rpm). With continued stirring (150 rpm) and continued heating to 60° C., 669 g of an iron(III) nitrate nonahydrate melt at 60° C. (13.6% by weight of Fe, <0.4% by weight of alkali metals, <0.01% by weight of chloride, <0.02% by weight of sulfate, from Dr. Paul Lohmann GmbH, D-81857 Emmerthal) were metered in, and the mixture was stirred (150 rpm) at 60° C. for a further 10 min. While maintaining the 60° C. and with continued stirring (150 rpm), 25.5 g of copper(II) nitrate hydrate (21.7% by weight of Cu) from Sigma-Aldrich Chemie GmbH, Munich, at a temperature of 25° C. were added to the resulting aqueous solution, and then the mixture was stirred (150 rpm) at 60° C. for a further 10 min. 631 g of an aqueous bismuth nitrate solution in nitric acid at 60° C. (10.8% by weight of Bi, 13% by weight of nitrate ($NO^{3-}$), prepared by dissolving bismuth metal from Sidech S.A., BE-1495 Tilly, purity >99.997% by weight of Bi, <7 mg/kg Pb, <5 mg/kg each of Ni, Ag, Fe, <3 mg/kg each of Cu, Sb, and <1 mg/kg each of Cd, Zn, in aqueous nitric acid) were added to the resulting aqueous solution, and the mixture was then stirred (150 rpm) at 60° C. for another 10 minutes.

c) Mixing of Aqueous Solution A with Aqueous Ssolution B

Aqueous solution A at 60° C. was metered with the aid of a peristaltic pump (model: BVP, supplier: Ismatec SA, Labortechnik-Analytik, Feldeggstrasse 6, CH-8152 Glattbrugg, setting: 320 scale divisions) continuously into aqueous solution B that had been kept warm at 60° C. and was now being stirred vigorously with an Ultra-Turrax (from Janke & Kunkel GmbH & Co.KG-IKA-Labortechnik, Janke & Kunkel-Str. 10, DE-79219 Staufen, shaft type: 550KR-G45 fine, shaft tube diameter: 25 mm, stator diameter: 45 mm, rotor diameter: 40 mm, setting: level 5) within 15 min. Aqueous solution A was introduced at the level of the rotor of the Ultra-Turrax stirrer, offset by about 0.5 to 1 cm from the outer edge of the rotor of the Ultra-Turrax stirrer. The resultant aqueous suspension was stirred at 60° C. for another 15 min.

d) Addition of a Silica Sol to Obtain an Aqueous Mixture M

Immediately after the further stirring had ended, 100 g of silica gel from Grace GmbH & KG, In der Hollerecke 1, D-67545 Worms, of the LUDOX TM50 type, that had been heated to 60° C. were then added to the aqueous mixture obtained in "c)", and then stirring was continued with the Ultra-Turrax at 60° C. for a further 15 min.

e) Spray Drying of the Aqueous Mixture M

The aqueous mixture M was spray-dried immediately after its production. The aqueous mixture (suspension) M, stirring of which was continued in each case (even during spray drying) at 60° C. by means of the anchor stirrer (150 rpm), was spray-dried in a spray tower of the Mobile Minor™ 2000 (MM-I) type from Niro NS, Gladsaxevej 305, 2860 Søborg, Denmark, having a centrifugal atomizer of the FOIA type and an atomizer wheel of the SL24-50 type in a hot air cocurrent flow (gas inlet temperature: 350±10° C., gas outlet temperature: 140±5° C., throughput: 4.7 kg of aqueous mixture M/h and a hot air stream at a flow rate of 8.5 $m^3$ (STP)/h). Constant stirring of the proportion of the aqueous mixture M that was yet to be spray-dried was continued at 60° C. The speed setting for the atomizer wheel was 25 000 rpm. The resultant spray powder was stored intermediately until further processing in airtight containers (capacity 200 L, 25° C., atmospheric pressure) (for 10 calendar days; shorter or longer intermediate storage (for up to 30 calendar days) had no effect on the resulting outcomes). The ignition loss of the spray powder obtained (calcine at 600° C. (powder temperature) under stationary air (present in excess) for 3 h) was 31% by weight of its starting weight.

f) Production of Ringlike Shaped Unsupported Catalyst Precursor Bodies

1% by weight of finely divided graphite of the TIMREX T44 brand from Timcal Ltd., CH-6743 Bodio (see WO 2008/087116), based on its weight, was mixed in homogeneous distribution into the resultant spray powder in a drum hoop mixer (wheel diameter: 650 mm, drum volume: 5 L) (speed: 30 rpm, mixing-in time: 30 min). The resulting homogeneous mixture was then compacted in a laboratory calender having 2 counter-rotating steel rolls (roll diameter 10 cm; roll length used for intermediate compaction: 13.5 cm; roll speed: 10 rpm) at a pressure of 9 bar and subsequently pushed through a stainless steel screen (grid) with square meshes (edge length=0.8 mm). A further 2.5% by weight of the same finely divided graphite, based on its weight, was mixed into the spray powder, coarsened as described, in the drum hoop mixer already described above (30 rpm, mixing-in time 30 minutes). Subsequently, the finely divided intimate dry mixture obtained, as described in DE-A 102008040093 (see example III of DE-A 102008040093) was compacted (tableted) to ringlike shaped unsupported catalyst precursor bodies of geometry E×H× I=5 mm×3 mm×2 mm with an uncurved (i.e. planar) end face and of mass (Mv) of 119 mg with a Kilian rotary tableting press (9-tablet tableting machine) of the S100 type (Kilian, D-50735 Cologne) under dried air and at ambient temperature of 25° C. The compression force Pv (main compression force) was 2.2 kN. The reservoir was filled with the finely divided intimate dry mixture up to a fill height (Hv) of 9.5 mm. The side crushing strength (SDFv) of the resulting ringlike shaped multimetal oxide precursor bodies was 29 N.

g) Thermal Pretreatment and Calcination of the Ringlike Shaped Unsupported Catalyst Precursor Bodies Produced in f)

1000 g of the shaped unsupported catalyst precursor bodies produced, divided equally between 4 mesh grids arranged alongside one another and each having a square base area of 150 mm×150 mm (bed height: 15 mm), were applied in an air circulation shaft oven (from Nabertherm GmbH, D-28865 Lilienthal; oven model: S60/65A) with a flow of 4500 L (STP)/h of predried air (at an inlet temperature of 140° C.) (the air circulation oven was in an environment at 25° C.). Subsequently, while maintaining the air flow (including its inlet temperature), the temperature in the air circulation shaft oven was varied as follows (the temperature figures mean the temperature in the bulk material applied in each case; these were determined by means of 4 thermocouples, each of which was in the geometric middle of the 4 mesh grids in the center of the bulk material applied to the respective mesh grid; one of the thermocouples provided the actual value for temperature control of the air circulation shaft oven; the other thermocouples confirmed that the temperatures were identical within the ±0.1° C. interval). The temperature increases were essentially linear over time. Heating was effected from 25° C. to 130° C. within 72 min. This temperature was maintained for 72 min and then increased to 190° C. within 36 min. The temperature was kept at 190° C. for 72 min before being increased to 220° C. within 36 min. The temperature was kept at 220° C. for 72 min before being increased to 265° C. within 36 min. The temperature was kept at 265° C. for 72 min before being increased to 380° C. within 93 min. The temperature was kept at 380° C. for 187 min before being increased to 430° C. within 93 min. The temperature was kept at 430° C. for 187 min before being increased to the final calcination temperature of 480° C. within 93 min. This was maintained for 463 min. Then cooling was effected to 25° C. within 12 h. For this purpose, both the heating of the air circulation shaft oven and the air stream preheating were switched off (however, the air stream of 4500 L (STP)/h itself was maintained; the inlet temperature of the air stream was then 25° C.). Until they were used for catalysis of heterogeneously catalyzed partial oxidation (for example of propene to acrolein), the ringlike shaped unsupported catalyst bodies E1 obtained were stored in an airtight container at a temperature of 25° C. and at atmospheric pressure.

2. Production of Shaped Unsupported Catalyst body E2

The production of shaped unsupported catalyst body E2 was effected in the same way as the production of shaped unsupported catalyst body E1. The starting weight stoichiometry present in the aqueous mixture M was likewise the stoichiometry $Mo_{12}Bi_{0.6}Fe_3Cu_{0.1}Co_7K0.08Si_{1.6}$. However, the final calcination temperature was 500° C.

3. Production of Shaped Unsupported Catalyst body E3

The production of shaped unsupported catalyst body E3 was effected in the same way as the production of shaped unsupported catalyst body E1. However, the added amounts of the sources of the elemental constituents other than Mo were matched to the starting weight stoichiometry $Mo_{12}Bi_{0.6}Fe_3Cu_{0.2}Co_7K_{0.08}Si_{1.6}$ present in the aqueous mixture M. The tableting conditions were as follows:

$M_T$=119 mg $P_T$=1.7 kN $H_T$=10 mm $SDF_T$=27 N

4. Production of Shaped Unsupported Catalyst body E4

The production of shaped unsupported catalyst body E4 was effected in the same way as the production of shaped unsupported catalyst body E1. However, the added amounts of the sources of the elemental constituents other than Mo were matched to the starting weight stoichiometry $Mo_{12}Bi_{0.6}Fe_3Cu_{0.2}Co_7K_{0.08}Si_{1.6}$ present in the aqueous mixture M and the final calcination temperature was 500° C.
The tableting conditions were as follows:

$M_T$=119 mg $P_T$=1.7 kN $H_T$=10 mm $SDF_T$=27 N

5. Production of Shaped Unsupported Catalyst Body E5

The production of shaped unsupported catalyst body E5 was effected in the same way as the production of shaped unsupported catalyst body E1. However, the added amounts of the sources of the elemental constituents other than Mo were matched to the starting weight stoichiometry $Mo_{12}Bi_{0.6}Fe_3Cu_{0.2}Co_7K_{0.08}Si_{1.6}$ present in the aqueous mixture M and the final calcination temperature was 520° C.
The tableting conditions were as follows:

$M_T$=119 mg $P_T$=2.5 kN $H_T$=9.9 mm $SDF_T$=18-28 N

6. Production of Shaped Unsupported Catalyst Body E6

The production of shaped unsupported catalyst body E6 was effected in the same way as the production of shaped unsupported catalyst body E1. However, the added amounts of the sources of the elemental constituents other than Mo were matched to the starting weight stoichiometry $Mo_{12}Bi_{0.6}Fe_3Cu_{0.4}Co_7K_{0.08}Si_{1.6}$ present in the aqueous mixture M and the final calcination temperature was 500° C.
The tableting conditions were as follows:

$M_T$=119 mg $P_T$=1.5 kN $H_T$=9.2 mm $SDF_T$=18-28 N

7. Production of Shaped Unsupported Catalyst Body E7

The production of shaped unsupported catalyst body E7 was effected in the same way as the production of shaped unsupported catalyst body E1. However, the added amounts of the sources of the elemental constituents other than Mo were matched to the starting weight stoichiometry $Mo_{12}Bi_{0.6}Fe_3Cu_{0.2}Co_7W_{0.2}K_{0.08}Si_{1.6}$ present in the aqueous mixture M and the final calcination temperature was 460° C. The source used for the element W dissolved in aqueous solution B was ammonium paratungstate (72% by weight of W, H.C. Starck, D-38642 Goslar). The ammonium paratungstate $((NH_4)_{10}(H_2W_{12}O_{24}) \times 4H_2O)$ was added to aqueous solution B while stirring (anchor stirrer, 150 rpm) at a solution temperature of 60° C. immediately after the addition to and the dissolution of the ammonium heptamolybdate tetrahydrate in aqueous solution B had ended. On completion of addition of the ammonium paratungstate, while maintaining the solution temperature of 60° C., stirring was continued (150 rpm) for another 20 min.
The tableting conditions were as follows:

$M_T$=119 mg $P_T$=1.0 kN $H_T$=8 mm $SDF_T$=22 N

8. Production of Shaped Unsupported Catalyst body E8

The production of shaped unsupported catalyst body E8 was effected in the same way as the production of shaped unsupported catalyst body E1. However, the added amounts of the sources of the elemental constituents other than Mo were matched to the starting weight stoichiometry $Mo_{12}Bi_{0.6}Fe_3Cu_{0.2}Co_7W_{0.2}K_{0.08}Si_{1.6}$ present in the aqueous mixture M. The source used for the element W dissolved in aqueous solution B was ammonium paratungstate (72% by weight of W, H. C. Starck, D-38642 Goslar). The ammonium paratungstate $((NH_4)_{10}(H_2W_{12}O_{24}) \times 4H_2O)$ was added to aqueous solution B while stirring (anchor stirrer, 150 rpm) at a solution temperature of 60° C. immediately after the addition to and the dissolution of the ammonium heptamolybdate tetrahydrate in aqueous solution B had ended. On completion of addition of the ammonium paratungstate, while maintaining the solution temperature of 60° C., stirring was continued (150 rpm) for another 20 min.

The tableting conditions were as follows:

$M_T$=119 mg $P_T$=1.0 kN $H_T$=8 mm $SDF_T$=22 N

9. Production of Comparative Shaped Unsupported Catalyst Body C4

The production of comparative shaped unsupported catalyst body C4 was effected in the same way as the production of shaped unsupported catalyst body E2. However, the starting weight stoichiometry present in the aqueous mixture M was the stoichiometry $Mo_{12}Bi_{0.6}Fe_3Co_7K_{0.08}Si_{1.6}$. This means that no Cu source was added in the production of aqueous solution A.

The tableting conditions were as follows:

$M_T$=119 mg $P_T$=2.5 kN $H_T$=11 mm $SDF_T$=26 N

10. Production of Comparative Shaped Unsupported Catalyst Body C5

The production of comparative shaped unsupported catalyst body C5 was effected in the same way as the production of comparative shaped unsupported catalyst body C4, except that the final calcination temperature was 520° C. The starting weight stoichiometry present in the aqueous mixture M was thus the stoichiometry $Mo_{12}Bi_{0.6}Fe_3Co_7K_{0.08}Si_{1.6}$.

11. Production of Comparative Shaped Unsupported Catalyst Body C6

The production of comparative shaped unsupported catalyst body C6 was effected in the same way as the production of comparative shaped unsupported catalyst body C4, except that the added amounts of the sources of the elemental constituents other than Mo were matched to the starting weight stoichiometry $Mo_{12}Bi_{0.65}Fe3.27Co_{7.64}K_{0.087}Si_{1.75}$ present in the aqueous mixture M.

The tableting conditions were as follows:

$M_T$=119 mg $P_T$=1.7 kN $H_T$=12.8 mm $SDF_T$=24 N

12. Production of Comparative Shaped Unsupported Catalyst Body C7

The production of comparative shaped unsupported catalyst body C7 was effected in the same way as the production of comparative shaped unsupported catalyst body C4, except that the added amounts of the sources of the elemental constituents other than Mo were matched to the starting weight stoichiometry $Mo_{12}Bi_{0.65}Fe_{3.27}Co_{7.64}K_{0.87}Si_{1.75}$ present in the aqueous mixture M and the final calcination temperature was 520° C.

The tableting conditions were as follows:

$M_T$=119 mg $P_T$=1.7 kN $H_T$=12.8 mm $SDF_T$=24 N

13. Production of Comparative Shaped Unsupported Catalyst Body C8

The production of comparative shaped unsupported catalyst body C8 was effected in the same way as the production of comparative shaped unsupported catalyst body C4, except that the added amounts of the sources of the elemental constituents other than Mo were matched to the starting weight stoichiometry $Mo_{12}Bi_{0.55}Fe_{2.77}Co_{6.46}K_{0.074}Si_{1.48}$ present in the aqueous mixture M and the final calcination temperature was 480° C.

The tableting conditions were as follows:

$M_T$=119 mg $P_T$=1.7 kN $H_T$=12.3 mm $SDF_T$=28 N

14. Production of Comparative Shaped Unsupported Catalyst Body C9

The production of comparative shaped unsupported catalyst body C9 was effected in the same way as the production of comparative shaped unsupported catalyst body C4, except that the added amounts of the sources of the elemental constituents other than Mo were matched to the starting weight stoichiometry $Mo_{12}Bi_{0.55}Fe_{2.77}Co_{6.46}K_{0.074}Si_{1.48}$ present in the aqueous mixture M and the final calcination temperature was 460° C.

The tableting conditions were as follows:

$M_T$=119 mg $P_T$=1.7 kN $H_T$=12.3 mm $SDF_T$=28 N

15. Production of Comparative Shaped Unsupported Catalyst Body C10

The production of comparative shaped unsupported catalyst body C10 was effected in the same way as the production of comparative shaped unsupported catalyst body C4, except that the added amounts of the sources of the elemental constituents other than Mo were matched to the starting weight stoichiometry $Mo_{12}Bi_{0.6}Fe_3Co_8K_{0.08}Si_{1.6}$ present in the aqueous mixture M and the final calcination temperature was 520° C.

The tableting conditions were as follows:

$M_T$=119 mg $P_T$=1-3 kN $H_T$=8-13 mm $SDF_T$=18-28 N

16. Production of Comparative Shaped Unsupported Catalyst Body C11

The production of comparative shaped unsupported catalyst body C11 was effected in the same way as the production of comparative shaped unsupported catalyst body C4, except that the added amounts of the sources of the elemental constituents other than Mo were matched to the starting weight stoichiometry $Mo_{12}Bi_{0.6}Fe_2Co_{8.5}K_{0.08}Si_{1.6}$ present in the aqueous mixture M and the final calcination temperature was 520° C.

The tableting conditions were as follows:

$M_T$=119 mg $P_T$=1.9 kN $H_T$=8-13 mm $SDF_T$=26 N

17. Production of Comparative Shaped Unsupported Catalyst Body C12

The production of comparative shaped unsupported catalyst body C12 was effected in the same way as the production of comparative shaped unsupported catalyst body C4, except that the added amounts of the sources of the elemental constituents other than Mo were matched to the starting weight stoichiometry $Mo_{12}Bi_{0.6}Fe_2Co_{8.5}K_{0.08}Si_{1.6}$ present in the aqueous mixture M.

The tableting conditions were as follows:

$M_T$=119 mg $P_T$=2.5 kN $H_T$=11.7 mm $SDF_T$=32 N

18. Production of Comparative Shaped Unsupported Catalyst Body C13

The production of comparative shaped unsupported catalyst body C13 was effected in the same way as the production of comparative shaped unsupported catalyst body C4, except that the added amounts of the sources of the elemental constituents other than Mo were matched to the starting weight stoichiometry $Mo_{12}Bi_{0.6}Fe_{3.5}Co_6K_{0.08}Si_{1.6}$ present in the aqueous mixture M.

The tableting conditions were as follows:

$M_T$=119 mg $P_T$=2.5 kN $H_T$=11.7 mm $SDF_T$=32 N

19. Production of Comparative Shaped Unsupported Catalyst Body C14

The production of comparative shaped unsupported catalyst body C14 was effected in the same way as the production of comparative shaped unsupported catalyst body C4, except that the added amounts of the sources of the elemental constituents other than Mo were matched to the starting weight stoichiometry $Mo_2Bi_{0.6}Fe_{2.5}Co_7K_{0.08}Si_{1.6}$ present in the aqueous mixture M and the final calcination temperature was 480° C.

The tableting conditions were as follows:

$M_T$=119 mg $P_T$=1 kN $H_T$=8.8 mm $SDF_T$=23 N

20. Production of Comparative Shaped Unsupported Catalyst Body C15

The production of comparative shaped unsupported catalyst body C15 was effected in the same way as the production of comparative shaped unsupported catalyst body C4, except that the added amounts of the sources of the elemental constituents other than Mo were matched to the starting weight stoichiometry $Mo_{12}Bi_{0.6}Fe_{3.5}Co_7K_{0.08}Si_{1.6}$ present in the aqueous mixture M and the final calcination temperature was 520° C.

The tableting conditions were as follows:

$M_T$=119 mg $P_T$=1.6 kN $H_T$=8-13 mm $SDF_T$=24 N

21. Production of Comparative Shaped Unsupported Catalyst Body C16

The production of comparative shaped unsupported catalyst body C16 was effected in the same way as the production of comparative shaped unsupported catalyst body C4, except that the added amounts of the sources of the elemental constituents other than Mo were matched to the starting weight stoichiometry $Mo_{12}Bi_{0.6}Fe_3Co_{62}K_{0.08}Si1.6$ present in the aqueous mixture M and the final calcination temperature was 480° C.

The tableting conditions were as follows:

$M_T$=119 mg $P_T$=1.7 kN $H_T$=12.5 mm $SDF_T$=24 N

22. Production of Comparative Shaped Unsupported Catalyst Body C17

The production of comparative shaped unsupported catalyst body C17 was effected in the same way as the production of comparative shaped unsupported catalyst body C4, except that the added amounts of the sources of the elemental constituents other than Mo were matched to the starting weight stoichiometry $Mo_{12}Bi_{0.6}Fe_3Co_{6.2}K_{0.08}Si_{1.6}$ present in the aqueous mixture M and the final calcination temperature was 460° C.

The tableting conditions were as follows:

$M_T$=119 mg $P_T$=1.7 kN $H_T$=12.5 mm $SDF_T$=24 N

23. Production of Comparative Shaped Unsupported Catalyst Body C18

The production of comparative shaped unsupported catalyst body C18 was effected in the same way as the production of comparative shaped unsupported catalyst body C4, except that the added amounts of the sources of the elemental constituents other than Mo were matched to the starting weight stoichiometry $Mo_{12}Bi_{0.6}Fe_3Co_{5.5}K_{0.08}Si1.6$ present in the aqueous mixture M and the final calcination temperature was 460° C.

The tableting conditions were as follows:

$M_T$=119 mg $P_T$=1-3 kN $H_T$=8-13 mm $SDF_T$=18-28 N

24. Production of Comparative Shaped Unsupported Catalyst Body C19

The production of comparative shaped unsupported catalyst body C19 was effected in the same way as the production of comparative shaped unsupported catalyst body C4, except that the added amounts of the sources of the elemental constituents other than Mo were matched to the starting weight stoichiometry $Mo_{12}Bi_{0.8}Fe_3Co_{5.5}W_{1.6}K_{0.08}Si_{1.6}$ present in the aqueous mixture M and the final calcination temperature was 466° C. The source used for the element W dissolved in aqueous solution B was ammonium paratungstate (72% by weight of W, H.C. Starck, D-38642 Goslar). The ammonium paratungstate $((N_4)_{10}(H_2W_{12}O_{24})\times 4H_2O)$ was added to aqueous solution B while stirring (anchor stirrer, 150 rpm) at a solution temperature of 60° C. immediately after the addition to and the dissolution of the ammonium heptamolybdate tetrahydrate in aqueous solution B had ended. On completion of addition of the ammonium paratungstate, while maintaining the solution temperature of 60° C., stirring was continued (150 rpm) for another 20 min.

The tableting conditions were as follows:

$M_T$=119 mg $P_T$=2.1 kN $H_T$=12.5 mm $SDF_T$=27 N

25. Production of Comparative Shaped Unsupported Catalyst Body C20

The production of comparative shaped unsupported catalyst body C20 was effected in the same way as the production of comparative shaped unsupported catalyst body C4, except that the added amounts of the sources of the elemental constituents other than Mo were matched to the starting weight stoichiometry $Mo_{12}Bi_{0.8}Fe_3Co_{5.5}W_{1.6}K_{0.08}Si_{1.6}$ present in the aqueous mixture M and the final calcination temperature was 480° C. The source used for the element W dissolved in aqueous solution B was ammonium paratungstate (72% by weight of W, H.C. Starck, D-38642 Goslar). The ammonium paratungstate $((NH_4)_{10}(H_2W_{12}O_{24})\times 4H_2O)$ was added to aqueous solution B while stirring (anchor stirrer, 150 rpm) at a solution temperature of 60° C. immediately after the addition to and the dissolution of the ammonium heptamolybdate tetrahydrate in aqueous solution B had ended. On completion of addition of the ammonium paratungstate, while maintaining the solution temperature of 60° C., stirring was continued (150 rpm) for another 20 min.

The tableting conditions were as follows:

$M_T$=119 mg $P_T$=1-3 kN $H_T$=8-13 mm $SDF_T$=18-28 N

26. Production of Comparative Shaped Unsupported Catalyst Body C21

The production of comparative shaped unsupported catalyst body C21 was effected in the same way as the production of shaped unsupported catalyst body E2, except that the added amounts of the sources of the elemental constituents other than Mo were matched to the starting weight stoichiometry $Mo_{12}Bi_{0.6}Fe_3Cu_{0.6}Co_7K0.08Si_{1.6}$ present in the aqueous mixture M.

The tableting conditions were as follows:

$M_T$=119 mg $P_T$=1.9 kN $H_T$=9.5 mm $SDF_T$=26 N

27. Production of Comparative Shaped Unsupported Catalyst Body C22

The production of comparative shaped unsupported catalyst body C22 was effected in the same way as the production of shaped unsupported catalyst body E2, except that the added amounts of the sources of the elemental constituents other than Mo were matched to the starting weight stoichiometry $Mo_{12}Bi_{0.6}Fe_3Cu_{0.6}Co_7K_{0.08}Si_{1.6}$ present in the aqueous mixture M and the final calcination temperature was 480° C.

The tableting conditions were as follows:

$M_T$=119 mg $P_T$=1.9 kN $H_T$=8.5 mm $SDF_T$=26 N

28. Production of Comparative Shaped Unsupported Catalyst Body C23

The production of comparative shaped unsupported catalyst body C23 was effected in the same way as the production of shaped unsupported catalyst body E2, except that the added amounts of the sources of the elemental constituents other than Mo were matched to the starting weight stoichiometry $Mo_{12}Bi_{0.6}Fe_3Cu_{0.8}Co_7K_{0.08}Si_{1.6}$ present in the aqueous mixture M.

The tableting conditions were as follows:

$M_T$=129 mg $P_T$=4.7 kN $H_T$=12.9 mm $SDF_T$=36 N

29. Production of Comparative Shaped Unsupported Catalyst Body C24

The production of comparative shaped unsupported catalyst body C24 was effected in the same way as the production of comparative shaped unsupported catalyst body C4, except that the added amounts of the sources of the elemental constituents other than Mo were matched to the starting weight stoichiometry $Mo_{12}B_{0.6}Fe_3Co_7K_{0.2}Si_{1.6}$ present in the aqueous mixture M.

The tableting conditions were as follows:

$M_T$=119 mg $P_T$=2.7 kN $H_r$=7.9 mm $SDF_r$=24 N

30. Production of Comparative Shaped Unsupported Catalyst Body C25

The production of comparative shaped unsupported catalyst body C25 was effected in the same way as the production of comparative shaped unsupported catalyst body C4, except that the added amounts of the sources of the elemental constituents other than Mo were matched to the starting weight stoichiometry $Mo_{12}Bi_{0.6}Fe_3Co_7K_{0.3}Si_{1.6}$ present in the aqueous mixture M.

The tableting conditions were as follows:

$M_r$=119 mg $P_r$=1.9 kN $H_r$=9.5 mm $SDF_r$=30 N

31. Production of Comparative Shaped Unsupported Catalyst Body C26

The production of comparative shaped unsupported catalyst body C26 was effected in the same way as the production of shaped unsupported catalyst body E2, except that the added amounts of the sources of the elemental constituents other than Mo were matched to the starting weight stoichiometry $Mo_{12}Bi_{0.6}Fe_3Co_7K_{0.08}$ present in the aqueous mixture M. This means that the aqueous mixture M did not comprise any added silica sol.

The tableting conditions were as follows:

$M_r$=119 mg $P_r$=2.1 kN $H_r$=7 mm $SDF_r$=21 N

32. Production of Comparative Shaped Unsupported Catalyst Body C27

The production of comparative shaped unsupported catalyst body C27 was effected in the same way as the production of comparative shaped unsupported catalyst body C4, except that the added amounts of the sources of the elemental constituents other than Mo were matched to the starting weight stoichiometry $Mo_{12}Bi_{0.6}Fe_3Co_7K_{0.08}Si_{3.2}$ present in the aqueous mixture M.

The tableting conditions were as follows:

$M_r$=119 mg $P_r$=2.3 kN $H_r$=8.3 mm $SDF_r$=29 N

33. Production of Comparative Shaped Unsupported Catalyst Body C28

The production of comparative shaped unsupported catalyst body C28 was effected in the same way as the production of comparative shaped unsupported catalyst body C4, except that the added amounts of the sources of the elemental constituents other than Mo were matched to the starting weight stoichiometry $Mo_{12}Bi_{1.2}Fe_3Co_7K_{0.08}Si_{1.6}$ present in the aqueous mixture M.

The tableting conditions were as follows:

$M_r$=119 mg $P_r$=1.7 kN $H_r$=10 mm $SDF_r$=27 N

34. Production of Comparative Shaped Unsupported Catalyst Body C29

The production of comparative shaped unsupported catalyst body C29 was effected in the same way as the production of comparative shaped unsupported catalyst body C4, except that the added amounts of the sources of the elemental constituents other than Mo were matched to the starting weight stoichiometry $Mo_{12}Bi_{1.2}Fe_3Co_7K_{0.08}Si_{1.6}$ present in the aqueous mixture M and the final calcination temperature was 520° C.

The tableting conditions were as follows:

$M_r$=119 mg $P_r$=1.7 kN $H_r$=10 mm $SDF_r$=27 N

35. Production of Comparative Shaped Unsupported Catalyst Body C30

The production of comparative shaped unsupported catalyst body C30 was effected in the same way as the production of comparative shaped unsupported catalyst body C4, except that the added amounts of the sources of the elemental constituents other than Mo were matched to the starting weight stoichiometry $Mo_{12}Bi_{1.8}Fe_3Co_7K_{0.08}Si_{1.6}$ present in the aqueous mixture M.

The tableting conditions were as follows:

$M_r$=119 mg $P_r$=1.1 kN $H_r$=9.1 mm $SDF_r$=20 N

36. Production of Comparative Shaped Unsupported Catalyst Body C31

The production of comparative shaped unsupported catalyst body C31 was effected in the same way as the production of comparative shaped unsupported catalyst body C4, except that the added amounts of the sources of the elemental constituents other than Mo were matched to the starting weight stoichiometry $Mo_{12}Bi_{1.8}Fe_3Co_7K_{0.08}Si_{1.6}$ present in the aqueous mixture M and the final calcination temperature was 520° C.

The tableting conditions were as follows:

$M_r$=119 mg $P_r$=1.1 kN $H_r$=9.1 mm $SDF_r$=20 N

37. Preparation of the comparative shaped unsupported catalyst body C1 wherein the active multimetal oxide has the stoichiometry $Mo_{12}Bi_{0.6}Fe_3Co_7K_{0.08}Si_{1.6}$ (stoichiometry by starting weight present in the aqueous mixture M)

The stirred vessels used were each filled in the presence of ambient air. In the course of stirring/mixing, they were sealed airtight with a lid that had a pressure release valve to the atmosphere (1 atm, 1.01 bar).

a) Preparation of an Aqueous Solution B

A temperature-controllable stainless steel (EN 1.4541) cylindrical stirred tank (internal diameter: 1.3 m; height: 1.9 m) equipped with an anchor stirrer was initially charged with 432 L of demineralized water and heated to 60° C. while stirring (70 rpm).

Subsequently, with constant stirring and while maintaining the temperature of 60° C., 0.45 kg of a 46.8% by weight aqueous potassium hydroxide solution (46.8% by weight of KOH) that had a temperature of 20° C. were added within one minute. While maintaining the 60° C., with constant stirring, 139.9 kg of fine granular ammonium heptamolybdate tetrahydrate at a temperature of 25° C. (supplier: NIPPON INORGANIC COLOUR & CHEMICAL CO., LTD., 3-14-1 Funado Itabashi-ku Tokyo 174-0041 (JP); it had a turbidity, determined to WO 2016/147324 of 219 NTU) were then stirred in in portions and the resulting aqueous solution (which was slightly turbid as a result of a tiny amount of insoluble isopolymolybdate contaminants) was stirred (70 rpm) at 60° C. for a further 90 min.

b) Preparation of an Aqueous Solution A

A temperature-controllable cylindrical stainless steel (EN 1.4541) stirred tank (internal diameter: 1.3 m; height: 1.9 m) equipped with an anchor stirrer was initially charged with 222.3 kg of an aqueous cobalt(II) nitrate solution in nitric acid (12.4% by weight of Co, 27% by weight of nitrate ($NO_3^-$), prepared by dissolving cobalt metal from MFT Metals % Ferro-Alloys Trading GmbH, D-41474 Viersen, purity >99.6% by weight of Co, <0.3% by weight of Ni, <100 mg/kg Fe, <50 mg/kg Cu in aqueous nitric acid), which were heated to 60° C. while stirring (70 rpm). With continued stirring (70 rpm) and continued heating to 60° C., 82.3 kg of an iron(III) nitrate nonahydrate melt at 60° C. (13.6% by weight of Fe, <0.4% by weight of alkali metals, <0.01% by weight of chloride, <0.02% by weight of sulfate, from Dr. Paul Lohmann GmbH, D-81857 Emmerthal) were metered in, and the mixture was stirred (70 rpm) at 60° C. for a further 30 min. With continued stirring (70 rpm), 77.6 kg of an aqueous bismuth nitrate solution in nitric acid at 60° C. (10.8% by weight of Bi, 13% by weight of nitrate ($NO^{3-}$), prepared by dissolving bismuth metal from Sidech S.A., BE-1495 Tilly, purity >99.997% by weight of Bi, <7 mg/kg Pb, <5 mg/kg each of Ni, Ag, Fe, <3 mg/kg each of Cu, Sb, and <1 mg/kg each of Cd, Zn, in aqueous nitric acid) were added to the resulting aqueous solution, and the mixture was then stirred (150 rpm) at 60° C. for another 30 minutes.

c) Mixing of Aqueous Solution A with Aqueous Solution B

Within 15 minutes, aqueous solution A at 60° C. was stirred into aqueous solution B at 60° C. (200 rpm). Thereafter, the emptied stirred tank that contained aqueous solution A was rinsed out with 5 L of demineralized water at 60° C. and the resultant rinse solution at 60° C. was then added all at once to the mixture of aqueous solution A and aqueous solution B at 60° C. and then the mixture was stirred while maintaining the 60° C. for another 15 minutes (150 rpm).

d) Addition of a Silica Sol to Obtain an Aqueous Mixture M

Immediately after the further stirring had ended, 12.3 kg of silica gel from Grace GmbH & KG, In der Hollerecke 1, D-67545 Worms, of the LUDOX TM50 type, that had been heated to 60° C. were added to the aqueous mixture obtained in "c)", and then stirring was continued with the anchor stirrer at 60° C. for a further 15 min (70 rpm).

e) Spray Drying of the Aqueous Mixture M

The aqueous mixture M was spray-dried immediately after its production. The aqueous mixture (suspension) M, stirring of which was continued in each case (even during spray drying) at 60° C. by means of the anchor stirrer (70 rpm), was spray-dried in a spray tower of the S-50-N/R type from Niro N S, Gladsaxevej 305, 2860 Søborg, Denmark, having a centrifugal atomizer of the FS-15 type and an atomizer wheel of the AM8-150 type in a hot air cocurrent flow (gas inlet temperature: 310±10° C., gas outlet temperature: 140±5° C., throughput: 550 kg/h of aqueous mixture M/h and hot air at 1800 m³ (STP)/h). Constant stirring of the proportion of the aqueous mixture M that was yet to be spray-dried was continued at 60° C. The speed setting for the atomizer wheel was 17 200 rpm. The resultant spray powder was stored intermediately until further processing in airtight containers (capacity 200 L, 25° C., atmospheric pressure) (for 15 calendar days; shorter or longer intermediate storage (for up to 30 calendar days) had no effect on the resulting outcomes). The ignition loss of the spray powder obtained (calcine at 600° C. (powder temperature) under stationary air (present in excess) for 3 h) was 33% by weight of its starting weight.

f) Production of Ringlike Shaped Unsupported Catalyst Precursor Bodies 100 kg of the spray powder thus obtained were mixed homogeneously with 1 kg of finely divided graphite of the Asbury 3160 brand from Asbury Graphite Mills, Inc. New Jersey 08802, USA (see WO 2008/087116) in an intensive mixer of the VIL-200 type from Aachener Misch- and Knetmaschinenfabrik Peter Kuppers GmbH & Co. KG, Veelser Strasse 71, D-52074 Aachen (intensive mixer with integrated blade heads, mixer speed: 540 rpm, translation ratio 1:3, blade head speed: 2800 rpm). The resulting dry mixture was coarsened by prior compaction to grain sizes in the range of 200 µm to 1.75 mm with a compactor (comprises a roll press with concave fluted smooth rollers, one conveying screw and three screens) from Hosokawa Bepex GmbH (D-74211 Leingarten) of the S655 compactor type under the conditions of gap width 2.8 mm, relief screen mesh size 1.0 mm, undersize screen mesh size 200 µm, oversize screen mesh size 1750 µm, target compression force 35 kN and screw speed 10 rpm. 300 kg of the spray powder coarsened as described and 6 kg of graphite of the Asbury 3160 brand were mixed homogeneously in an EMS 180 mixer from DRAISWERKE GmbH-Mannheim-Waldhof, Spezialmaschinenfabrik, Speckweg 43/53, D-Mannheim (the mixer ran at 20 rpm; the integrated blade heads were not in operation) within 5 minutes. Subsequently, the finely divided intimate dry mixture obtained, as described in DE-A 102008040093 (see example III of DE-A 102008040093) was compacted (tableted) to ringlike shaped unsupported catalyst precursor bodies of geometry E×H×I=5 mm×3 mm×2 mm with an uncurved (i.e. planar) end face and of mass ($M_V$) of 122 mg with a Kilian rotary tableting press (9-tablet tableting machine) of the S100 type (Kilian, D-50735 Cologne) under ambient air and at ambient temperature of 25° C. The compression force $P_V$ (main compression force) was 2.2 kN. The reservoir was filled with the finely divided intimate dry mixture up to a fill height ($H_V$) of 6.5 mm. The side crushing strength ($SDF_V$) of the resulting ringlike shaped multimetal oxide precursor bodies was 23 N.

g) Thermal Pretreatment and Calcination of the Ringlike Shaped Unsupported Catalyst Precursor Bodies Produced in f)

1000 g of the shaped unsupported catalyst precursor bodies produced, divided equally between 4 mesh grids arranged alongside one another and each having a square base area of 150 mm×150 mm (bed height: 15 mm), were applied in an air circulation shaft oven (from Nabertherm GmbH, D-28865 Lilienthal; oven model: S60/65A) with a flow of 4500 L (STP)/h of predried air (at an inlet temperature of 140° C.) (the air circulation oven was in an environment at 25° C.). Subsequently, while maintaining the air flow (including its inlet temperature), the temperature in the air circulation shaft oven was varied as follows (the temperature figures mean the temperature in the bulk material applied in each case; these were determined by means of 4 thermocouples, each of which was in the geometric middle of the 4 mesh grids in the center of the bulk material applied to the respective mesh grid; one of the thermocouples provided the actual value for temperature control of the air circulation shaft oven; the other thermocouples confirmed that the temperatures were identical within the ±0.1° C. interval). The temperature increases were essentially linear over time. Heating was effected from 25° C. to 130° C. within 72 min. This temperature was maintained for 72 min and then increased to 190° C. within 36 min. The temperature was kept at 190° C. for 72 min before being increased to 220° C. within 36 min. The temperature was kept at 220° C. for 72 min before being increased to 265° C. within 36 min. The temperature was kept at 265° C. for 72 min before being increased to 380° C. within 93 min. The temperature was kept at 380° C. for 187 min before being increased to 430° C. within 93 min. The temperature was kept at 430° C. for 187 min before being increased to the final calcination temperature of 500° C. within 93 min. This was maintained for 463 min. Then cooling was effected to 25° C. within 12 h. For this purpose, both the heating of the air circulation shaft oven and the air stream preheating were switched off (however, the air stream of 4500 L (STP)/h itself was maintained; the inlet temperature of the air stream was then 25° C.). Until they were used for catalysis of heterogeneously catalyzed partial oxidation (for example of propene to acrolein), the ringlike shaped unsupported catalyst bodies C1 obtained were stored in an airtight container at a temperature of 25° C. and at atmospheric pressure.

38. Production of Comparative Shaped Unsupported Catalyst body C2

The production of comparative shaped unsupported catalyst body C2 was effected in the same way as the production of comparative shaped unsupported catalyst body C1. However, the final calcination temperature was 480° C.

39. Production of Comparative Shaped Unsupported Catalyst Body C3

The production of comparative shaped unsupported catalyst body C3 was effected in the same way as the production of comparative shaped unsupported catalyst body C1. However, the final calcination temperature was 520° C.

II. Catalysis of a heterogeneously catalyzed partial gas phase oxidation of propene to acrolein (main product) and acrylic acid (by-product) with the ringlike shaped unsupported catalyst bodies produced in I.

A reaction tube (V2A steel, external diameter 21 mm, wall thickness 3 mm, internal diameter 15 mm, length 120 cm) was charged from the top downward (in the later flow direction of the reaction gas mixture) as follows:

Section 1: length 30 cm
    40 g of steatite spheres (C220 steatite from CeramTec) with a diameter of 1.5 to 2.0 mm as preliminary bed;

Section 2: length 70 cm
    Catalyst charge of 100 g of the respective ringlike shaped unsupported catalyst body produced in I.

The temperature of the reaction tube was controlled in each case by means of a molecular nitrogen-sparged salt melt (53% by weight of potassium nitrate, 40% by weight of sodium nitrite and 7% by weight of sodium nitrate). The salt bath (the salt melt) was within a cylindrical shell of internal diameter 11 cm. The cylindrical shell had the same length as the reaction tube. The latter was guided from the top downward within the cylindrical shell such that the two axes of symmetry coincided. The nitrogen flow rate bubbled into the salt bath from the bottom at a temperature of 25° C. was 40 L (STP)/h (standard conditions=1.01 bar, 0° C.). The heat losses from the salt bath to the environment were greater than the heat of reaction released to the salt bath by the tubular reactor during the partial oxidation. The salt bath was therefore kept at its temperature $T^{SB}$ (° C.) by means of electrical heating. In this way, it was ensured that the outer wall of the reaction tube was always at the appropriate temperature $T^{SB}$ (° C.).

The reaction tube was charged continuously with a reaction gas input mixture that had the following composition:
    5% by vol. of propene (of polymer grade purity),
    9.5% by vol. of molecular oxygen, and
    85.5% by vol. of molecular nitrogen.

The flow rate of the reaction gas input mixture stream fed to the reaction tube at a temperature of 150° C. was a constant 100 L (STP)/h. The pressure at the inlet into the reaction tube in all cases was 1.2 bar absolute (at the reaction tube outlet there was a control valve for the purpose of inlet pressure adjustment). In single pass of the reaction gas mixture through the reaction tube including control valve, the pressure drop thereof was 0.2 bar.

At the start of every partial oxidation experiment with a fresh fixed bed charge, $T^{SB}$ was set to a temperature of 325° C. For the first time after an operating time of 2 h at $T^{SB}$=325° C. and thereafter until attainment of a total operating time of 72 hours, on the basis of the gas chromatography analysis of the composition of the product gas mixture that results in each case and of the reaction gas input mixture guided into the reaction tube, the respective present propene conversion $C^P$ and the respective resulting selectivity of product of value formation $S^{PV}$ (each based on a single pass of the reaction gas mixture through the reaction tube) were determined every 2 h, and then the value of $T^{SB}$, proceeding from its existing magnitude in each case, was increased or lowered such that the propene conversion $C^P$, based on a single pass of the reaction gas mixture through the reaction tube, at the respective newly established value of $T^{SB}$ (immediately after resetting of $T^{SB}$) was 95 mol % in each case. The newly established value of $T^{SB}$ was then maintained unchanged for an operating period of 2 h in each case. The arithmetic average of the last 12 (i.e. in the total operating time interval of 48 h to 72 h) values of $T^{SB}$ (° C.) required in each case for a propene conversion $C^P$ (based on a single pass of the reaction gas mixture through the reaction tube) of 95 mol % is the value $T^{SBend}$ (° C.). This indicates the activity of the respective catalyst. The arithmetic average of the last 12 (i.e. in the total operating time interval of 48 h to 72 h) values determined for the product of value selectivity $S^{PV}$ (based on a single pass of the reaction gas mixture through the reaction tube) is the value $S^{PVend}$. This indicates the selectivity of product of value formation over the respective catalyst.

The composition of the reaction gas mixture was determined "on-line" by gas chromatography both at the inlet and at the outlet into the reaction tube.

The propene conversion ($C^P$ (mol %)) based on a single pass of the reaction gas mixture through the reaction tube was determined from the molar propene content $C^{Pin}$ of the reaction gas mixture at the reaction tube inlet and the molar propene content $C^{Pout}$ of the reaction gas mixture at the reaction tube outlet as follows:

$$C^P(\text{mol \%})=100\times(C^{Pin}-C^{Pout})/C^{Pin}.$$

The molar acrolein content of the reaction gas mixture ($C^{Aout}$) at the reaction tube outlet, the molar acrylic acid content of the reaction gas mixture ($C^{Sout}$) at the reaction tube outlet and $C^{Pin}$ and $C^{Pout}$ were used to determine the selectivity of acrolein formation ($S^A$ (mol %)) and of acrylic acid formation ($S^S$ (mol %)) based on a single pass of the reaction gas mixture through the reaction tube as follows:

$$S^A \text{ (mol \%)}=100\times(C^{Aout}/(C^{Pin}-C^{Pout}));$$

$$S^S(\text{mol \%})=100\times(C^{Sout}/(C^{Pin}-C^{Pout}))$$

The selectivity of overall product of value formation $S^{PV}$ (mol %) is calculated as the sum total of $S^A$ (mol %)+$S^S$ (mol %).

Table 1 shows the values of $T^{SBend}$ (° C.) and $S^{PVend}$ (mol %) determined as a function of the respective ringlike shaped unsupported catalyst body used. Smaller values of $T^{SBend}$ (° C.) reflect a higher activity of the catalyst used, and higher values of $S^{PVend}$ (mol %) reflect a higher selectivity of product of value formation over the catalyst used.

TABLE 1

| Shaped unsupported catalyst body | $T^{SBend}$ (° C.) | $S^{PVend}$ (mol %) |
|---|---|---|
| C1 | 307 | 93.9 |
| C2 | 306 | 92.9 |
| C3 | 317 | 95.8 |
| C4 | 310 | 94.9 |
| C5 | 318 | 96.5 |
| C6 | 303 | 93.7 |
| C7 | 308 | 94.6 |
| C8 | 318 | 94.4 |
| C9 | 305 | 94.0 |
| C10 | 310 | 94.5 |
| C11 | 328 | 96.6 |
| C12 | 315 | 95.2 |
| C13 | 322 | 95.6 |
| C14 | 317 | 95.8 |
| C15 | 315 | 95.5 |
| C16 | 315 | 95.0 |
| C17 | 304 | 93.3 |
| C18 | 310 | 93.9 |
| C19 | 304 | 92.6 |
| C20 | 319 | 94.9 |
| C21 | 317 | 94.5 |
| C22 | 300 | 93.0 |
| C23 | 304 | 91.9 |
| C24 | 322 | 96.4 |
| C25 | 327 | 96.1 |
| C26 | 326 | 96.4 |
| C27 | 315 | 94.9 |
| C28 | 309 | 94.2 |
| C29 | 318 | 95.6 |
| C30 | 309 | 93.5 |
| C31 | 321 | 95.6 |
| E1 | 310 | 96.0 |
| E2 | 328 | 96.9 |
| E3 | 303 | 96.0 |
| E4 | 312 | 96.6 |

TABLE 1-continued

| Shaped unsupported catalyst body | $T^{SBend}$ (° C.) | $S^{PVend}$ (mol %) |
|---|---|---|
| E5 | 317 | 96.6 |
| E6 | 308 | 96.4 |
| E7 | 306 | 95.4 |
| E8 | 315 | 96.4 |

The FIGURE shows a plot of the results shown in table 1 for the inventive shaped unsupported catalyst bodies (□) E1 to E8 and for the comparative shaped unsupported catalyst bodies (●) C1 to C31. The FIGURE shows selectivity of total product of value formation $S^{PVend}$ (mol %) plotted as the ordinate versus the salt bath temperature $T^{SBend}$ (° C.) required in each case for the target propene conversion of 95 mol % as the abscissa. The FIGURE shows clearly that the shaped unsupported catalyst bodies of the invention, given the same catalyst activity (same value of $T^{SBend}$), result in significantly higher selectivities $S^{PVend}$ (mol %) of total product of value formation.

The unsupported catalyst according to the working example of DE-A 102009047291 with the stoichiometry $[Bi_2W_2O_9.2W_3]_{0.40}[Mo_{12}Co_{5.4}Fe_{3.1}Si_{1.5}K_{0.08}O_x]_1$ (including the 15% by weight spall of this unsupported catalyst), used in the example and comparative example of WO 2012/049246, can be replaced by any of comparative unsupported catalysts C1 to C31 and by any of the illustrative shaped unsupported catalyst bodies E1 to E8 (including the 15% by weight of spall of the unsupported catalyst), and the comparative example or working example of WO 2012/049246 can otherwise be executed as described in WO 2012/049246.

It is likewise possible to replace the unsupported catalyst according to example 1 of DE-A 100 46 957 (stoichiometry: $[Bi_2W_2O_9\times2WO_3]_{0.5}$ $[Mo_{12}Co_{5.5}Fe_{2.94}Si_{1.59}K_{0.08}O_x]_1$), used in the first oxidation stage in the example of WO 2007/074045, by any of the comparative unsupported catalysts C1 to C31 and by any of the illustrative shaped unsupported catalyst bodies E1 to E8 (including the 15% by weight of spall of the unsupported catalyst) and to execute the example of WO 2007/074045 otherwise as described in WO 2007/074045.

In addition, the annular unsupported catalyst used in the first reaction stage of the partial oxidation executed by way of example in WO 2006/042459 can be replaced by any of the comparative unsupported catalysts C1 to C31 and by any of the illustrative shaped unsupported catalyst bodies E1 to E8 (including the spall of the unsupported catalyst) and this partial oxidation of WO 2006/042459 can otherwise be executed as described in WO 2006/042459.

The invention claimed is:

1. A multimetal oxide composition, comprising Mo, Bi, Fe and Cu and not comprising P, the multimetal oxide composition having the general stoichiometry (I):

$$Mo_{12}Bi_aFe_bCu_cCo_dNi_eW_fG_gH_hL_lM_mO_x \qquad (I),$$

wherein:
  G=at least one element selected from the group consisting of K, Na, Rb and Cs,
  H=at least one element selected from the group consisting of Ba, Ca, Cr, Ce, La, Mg, Mn, Pb, Sn, Sr and Zn,
  L=at least one element selected from the group consisting of B, Nb, Sb, Ta, Te, Ti, Y and Zr,
  M=at least one element selected from the group consisting of Al and Si, a=0.2 to 2.5,
b=0.5 to 4,
c=0.05 to 0.55,
d+e=4 to 11,
f=0 to 1.2,
g=0.03 to 0.5,
h=0 to 20,
l=0 to 10,
m=0 to 800,
x=a number which is determined by the valency and frequency of the elements in I other than oxygen, $12/(d+e+1.5*b+h)=0.8$ to 2, and $a*c=0.01$ to 1.5.

2. The multimetal oxide composition according to claim 1, wherein c=0.05 to 0.5.

3. The multimetal oxide composition according to claim 1, wherein c=0.05 to 0.45.

4. The multimetal oxide composition according to claim 1, wherein c=0.05 to 0.4.

5. The multimetal oxide composition according to claim 1, wherein c=0.05 to 0.35.

6. The multimetal oxide composition according to claim 1, wherein c=0.1 to 0.3.

7. An eggshell catalyst, comprising a shaped support body and an eggshell of at least one multimetal oxide composition according to claim 1 present on an outer surface of the shaped support body.

8. A shaped unsupported catalyst body, the active composition of which is at least one multimetal oxide composition according to claim 1.

9. The unsupported catalyst according to claim 8, having the geometry of a ring having a wall thickness of 1 to 3 mm, a length of 2 to 10 mm and an external diameter of 2 to 10 mm.

10. A process for producing the multimetal oxide composition according to claim 1, the process comprising:
producing a finely divided intimate dry mixture from sources of the elemental constituents thereof and calcining the finely divided intimate dry mixture at temperatures in the range from 350° C. to 650° C.

11. A process for heterogeneously catalyzed partial gas phase oxidation of an alkane, alkanol, alkanal, alkene and/or alkenal having 3 to 6 carbon atoms over a catalyst bed, the process comprising contacting the alkane, alkanal, alkene and/or alkenal having 3 to 6 carbon atoms with the catalyst bed,
wherein the catalyst bed comprises either:
at least one multimetal oxide composition according to claim 1,
at least one eggshell catalyst comprising a shaped support body and an eggshell of the at least one multimetal oxide composition present on an outer surface of the shaped support body,
at least one shaped unsupported catalyst body, the active composition of which is the at least one multimetal oxide composition, at least one shaped unsupported catalyst body having the geometry of a ring having a wall thickness of 1 to 3 mm, a length of 2 to 10 mm and an external diameter of 2 to 10 mm, and the active composition of which is the at least one multimetal oxide composition, or
the product of a process comprising producing a finely divided intimate dry mixture from sources of the elemental constituents thereof and calcining the finely divided intimate dry mixture at temperatures in the range from 350° C. to 650° C.

12. The process according to claim 11, which is a process for heterogeneously catalyzed partial gas phase oxidation of propene to acrolein.

13. The multimetal oxide composition according to claim 1, wherein m=0.1 to 500.

14. The multimetal oxide composition according to claim 1, wherein W is present.

15. The multimetal oxide composition according to claim 1, wherein at least one selected from the group of Cr, Ce, La, Mn, Pb, Sn, and Zn is present.

* * * * *

UNITED STATES PATENT AND TRADEMARK OFFICE
CERTIFICATE OF CORRECTION

PATENT NO. : 10,682,631 B2
APPLICATION NO. : 16/250244
DATED : June 16, 2020
INVENTOR(S) : Kazuhiko Amakawa et al.

It is certified that error appears in the above-identified patent and that said Letters Patent is hereby corrected as shown below:

In the Specification

Column 3, Line 58, "$Q^2=1$" should read --$Q^2=1$.--

Column 5, Line 33, "(generally" should read --generally--

Column 7, Line 16, "Nat" should read --$Na^+$--

Column 7, Line 25, "Hollerecke" should read --Hollerhecke--

Column 8, Line 61, "$(n_{No3-})/(n_{Bi3+})$" should read --$(n_{No}^{3-})/(n_{Bi}^{3+})$--

Column 8, Line 61, "$n_{No3-}$" should read --$n_{No}^{3-}$--

Column 8, Line 63, "$n_{Bi3+}$" should read --$n_{Bi}^{3+}$--

Column 8, Line 63, ">3)" should read -->3--

Column 9, Line 46, "$Cu(NO_3)_2$" should read --$Cu(NO_3^-)_2$--

Column 15, Line 28, "1%" should read --≤1%--

Column 17, Line 15, "and" should read --und--

Column 20, Line 47, "and" should read --und--

Column 22, Line 1, "preferably ÷" should read --preferably≥--

Column 23, Line 53, ">70%" should read --≥70%--

Signed and Sealed this
First Day of December, 2020

Andrei Iancu
*Director of the United States Patent and Trademark Office*

CERTIFICATE OF CORRECTION (continued)
U.S. Pat. No. 10,682,631 B2

Column 26, Line 10, "Cert" should read --tert--

Column 26, Line 16, "charge)" should read --charge--

Column 27, Line 32, "or:" should read --or--

Column 32, Line 38, "80" should read --$\geq$80--

Column 32, Line 39, "85" should read --$\geq$85--

Column 37, Line 20, "cm3/g" should read --cm$^3$/g--

Column 37, Line 35, "70%" should read --$\geq$70--

Column 45, Line 9, "NO3$^-$" should read --NO$_3^-$--

Column 45, Line 35, "Ssolution" should read --Solution--

Column 45, Line 43, "Co.KG" should read --Co. KG--

Column 45, Line 55, "Hollerecke" should read --Hollerhecke--

Column 46, Line 1, "FOIA" should read --FO1A--

Column 47, Line 32, "K0.08" should read --K$_{0.08}$--

Column 47, Line 40, "C$_{07}$" should read --Co$_7$--

Column 49, Line 52 (approx.), "Fe3.27" should read --Fe$_{3.27}$--

Column 50, Line 3, "K$_{0.87}$" should read --K$_{0.087}$--

Column 51, Line 61 (approx.), "Mo$_2$" should read --Mo$_{12}$--

Column 52, Line 30, "Co$_{62}$K$_{0.08}$Si1.6" should read --Co$_{6.2}$K$_{0.08}$Si$_{1.6}$--

Column 53, Line 1, "Si1.6" should read --Si$_{1.6}$--

Column 53, Line 24 (approx.), "N$_4$" should read --NH$_4$--

Column 54, Line 8, "K0.08" should read --K$_{0.08}$--

Column 54, Line 62 (approx.), "B$_{0.6}$" should read --Bi$_{0.6}$--

Column 57, Line 65, "Hollerecke" should read --Hollerhecke--

CERTIFICATE OF CORRECTION (continued)
U.S. Pat. No. 10,682,631 B2

Column 58, Line 9 (approx.), "N S" should read --A/S--

Column 58, Line 33 (approx.), "and" should read --und--

Column 58, Line 34 (approx.), "Kuppers" should read --Kupper--

Column 58, Line 35 (approx.), "Veelser" should read --Vaalser--

Column 59, Line 46, "Cl" should read --C1--

Column 61, Line 24 (approx.), "$C^{Pout}$))" should read --$C^{Pout}$)).--

Column 62, Line 23 (approx.), "$2W_3$" should read --$2WO_3$--